(12) United States Patent
Hagen et al.

(10) Patent No.: US 9,890,126 B2
(45) Date of Patent: Feb. 13, 2018

(54) SYNTHESIS OF NOVEL INHIBITORS OF ISOPRENOID BIOSYNTHESIS (ISPF)

(71) Applicants: BOARD OF TRUSTEES OF NORTHERN ILLINOIS UNIVERSITY, DeKalb, IL (US); BERYLLIUM DISCOVERY CORP., Bedford, MA (US)

(72) Inventors: Timothy J. Hagen, Lisle, IL (US); Zheng Zhang, Dekalb, IL (US); Zachary Lazowski, Lisle, IL (US); Michael Clare, Skokie, IL (US); Darren W. Begley, Seattle, WA (US)

(73) Assignees: Board of Trustees of Northern Illinois University, DeKalb, IL (US); Beryllium Discovery Corp., Bedford, MA (US)

( * ) Notice: Subject to any disclaimer, the term of this patent is extended or adjusted under 35 U.S.C. 154(b) by 0 days.

(21) Appl. No.: 15/065,571

(22) Filed: Mar. 9, 2016

(65) Prior Publication Data
US 2016/0257655 A1    Sep. 8, 2016

Related U.S. Application Data

(62) Division of application No. 14/390,548, filed as application No. PCT/US2013/037765 on Apr. 23, 2013, now Pat. No. 9,309,232.

(60) Provisional application No. 61/637,642, filed on Apr. 24, 2012, provisional application No. 61/701,269, filed on Sep. 14, 2012, provisional application No. 61/703,145, filed on Sep. 19, 2012.

(51) Int. Cl.
| | |
|---|---|
| *C07D 233/64* | (2006.01) |
| *C07D 403/12* | (2006.01) |
| *C07F 9/6571* | (2006.01) |
| *C07D 239/47* | (2006.01) |
| *C07D 417/12* | (2006.01) |
| *A61K 45/06* | (2006.01) |
| *A61K 31/4164* | (2006.01) |
| *A61K 31/506* | (2006.01) |
| *C07D 401/12* | (2006.01) |
| *C07D 403/06* | (2006.01) |
| *C07D 405/06* | (2006.01) |
| *C07D 405/12* | (2006.01) |
| *A61K 31/4174* | (2006.01) |
| *A61K 31/4178* | (2006.01) |
| *C07D 413/12* | (2006.01) |

(52) U.S. Cl.
CPC ........ *C07D 233/64* (2013.01); *A61K 31/4164* (2013.01); *A61K 31/4174* (2013.01); *A61K 31/4178* (2013.01); *A61K 31/506* (2013.01); *A61K 45/06* (2013.01); *C07D 239/47* (2013.01); *C07D 401/12* (2013.01); *C07D 403/06* (2013.01); *C07D 403/12* (2013.01); *C07D 405/06* (2013.01); *C07D 405/12* (2013.01); *C07D 417/12* (2013.01); *C07F 9/657136* (2013.01); *C07D 413/12* (2013.01)

(58) Field of Classification Search
CPC .. A61K 45/06; A61K 31/4178; A61K 31/506; A61K 31/4164; A61K 31/4174; A61K 2300/00; C07D 233/64; C07D 401/12; C07D 403/06; C07D 405/06; C07D 405/12; C07D 403/12; C07D 239/47; C07D 413/12; C07D 417/12; C07F 9/657136

See application file for complete search history.

(56) References Cited

U.S. PATENT DOCUMENTS

| | | | | |
|---|---|---|---|---|
| 4,218,458 A | * | 8/1980 | Heeres ............... | A01N 43/60 514/364 |
| 4,232,034 A | * | 11/1980 | Heeres ............... | C07D 231/12 514/382 |
| 4,244,964 A | * | 1/1981 | Heeres ............... | C07D 231/12 514/382 |
| 4,268,680 A | * | 5/1981 | Heeres ............... | C07D 231/12 548/311.1 |
| 4,447,422 A | | 5/1984 | Taylor | |
| 4,533,550 A | * | 8/1985 | Heeres ............... | A01N 43/60 514/256 |
| 4,666,915 A | | 5/1987 | Ozeki | |
| 7,429,665 B2 | * | 9/2008 | Verhoest .............. | C07D 413/14 546/152 |
| 7,825,254 B2 | * | 11/2010 | Verhoest .............. | C07D 413/14 546/176 |
| 2003/0004202 A1 | | 1/2003 | Elliott et al. | |
| 2003/0176430 A1 | * | 9/2003 | Take ..................... | C07C 45/71 514/230.5 |

(Continued)

FOREIGN PATENT DOCUMENTS

| | | |
|---|---|---|
| CA | 1218368 | 2/1987 |
| CH | 361283 | 4/1962 |

(Continued)

OTHER PUBLICATIONS

T, Najamura et al., 46Journal of Medicinal Chemistry, 5416-5427 (2003).*

(Continued)

*Primary Examiner* — Alexander R Pagano
(74) *Attorney, Agent, or Firm* — Barnes & Thornburg LLP; Alice O. Martin

(57) ABSTRACT

Antibacterial and antimalarial IspF inhibitor compounds and compositions are described. Methods include administering described compounds and compositions to treat bacterial or parasitic infections and to inhibit parasite or bacterial growth.

4 Claims, 11 Drawing Sheets

(56) References Cited

U.S. PATENT DOCUMENTS

| | | | |
|---|---|---|---|
| 2003/0176454 A1* | 9/2003 | Yamada | C07D 217/08 514/284 |
| 2006/0154931 A1* | 7/2006 | Verhoest | C07D 413/14 514/249 |
| 2007/0155779 A1* | 7/2007 | Verhoest | C07D 401/14 514/303 |
| 2008/0214607 A1* | 9/2008 | Verhoest | C07D 413/14 514/314 |
| 2011/0020460 A1* | 1/2011 | Mascitti | C07D 401/14 424/520 |
| 2011/0045101 A1* | 2/2011 | Selby | A01N 43/50 424/632 |
| 2011/0046142 A1* | 2/2011 | Lewis | A61K 31/34 514/246 |
| 2011/0136796 A1* | 6/2011 | Mautino | C07D 233/56 514/227.8 |

FOREIGN PATENT DOCUMENTS

| | | | |
|---|---|---|---|
| EP | 0067610 | 12/1982 | |
| EP | 0144730 | 6/1985 | |
| GB | 859716 | 1/1961 | |
| GB | 1208129 | * 10/1970 | C07D 231/12 |
| JP | S62-267229 | 11/1987 | |
| JP | H05-262747 | 10/1993 | |
| JP | 2004262890 A * | 9/2004 | |
| WO | WO-03022821 A1 * | 3/2003 | A61K 31/395 |
| WO | WO 2009/127615 | 10/2009 | |
| WO | WO-2009132238 A2 * | 10/2009 | C07D 233/56 |

OTHER PUBLICATIONS

B. Darvis, 54 Agricultural and Biological Chemistry, 3045-3047 (1990).*

E. Kuwano et al., 34 Pesticide Science, 263-268 (1992).*

Office Action issued in Application No. 13719691.1 (dated Oct. 13, 2016).

Aguirre et al, "Novel Antiprotoxoal Products: Imidazole and BenzimidazoleN-Oxide Derivatives and Related Compounds," *Archiv. Der Pharmazie*, 337(5): 259-270 (2004).

Badawey et al., 330 Archiv der Pharmazie (Weinheim, Germany), 59-62 (1997).

CAS Abstract 4,447,422 (1983).

CAS Abstract of CH 361,283 (1961).

CAS Reg No. 908544-55-8 (2006).

CAS Registry No. 861211-28-1 (Aug. 21, 2005).

Rostom et al., 7 Scientia Pharmaceutica, 57-74 (2003).

Search Report and Written Opinion issued in Int'l App. No. PCT/US2013/037765 (2013).

Second Written Opinion issued in Int'l App. No. PCT/US2013/037765 (2014).

Sorm et al, "Antitubercular activity of 2-amino-4-hydroxy-5-pyrimidinecarboxylic acid, pyrimidine analogue of p-aminosalicilic acid," *Chem. Listy. Pro Vedu a Prumysl*, 45: 422-423 (1951) (Abstract).

Stanovinik et al., 91 Advances in Heterocyclic Chemistry, 1-134 (2006).

Yurugi et al., 28 Takeda Kenkyusho Nenpo, 1-11 (1969).

U.S. Appl. No. 14/390,548, filed Oct. 3, 2014.

* cited by examiner

SYNTHESIS OF NOVEL INHIBITORS OF ISOPRENOID BIOSYNTHESIS (ISPF)

CROSS REFERENCE TO RELATED APPLICATIONS

This application is a Divisional of co-pending U.S. application Ser. No. 14/390,548, filed Oct. 3, 2014, which is a U.S. nationalization under 35 U.S.C. §371 of International Application No. PCT/US2013/037765, filed Apr. 23, 2013, which claims the benefit of priority under 35 U.S.C. § 119(e) to U.S. provisional application No. 61/637,642, filed Apr. 24, 2012, 61/701,269 filed Sep. 14, 2012 and 61/703,145, filed Sep. 19, 2012. The disclosures of the referenced applications are incorporated herein by reference in their entireties.

BACKGROUND

The fight against malaria, tuberculosis, and other infectious disease is growing more difficult due to the emergence of drug resistant forms of these diseases. One strategy to address the resistance problem is to develop novel anti-infective agents that employ new mechanisms of action. In recent studies, it has been shown that bacterial and parasitic organisms, such as those involved in malaria, tuberculosis, and melioidosis, use the methylerythritol isoprenoid (MEP) biosynthetic pathway, to produce isoprenoids, which are the basic building blocks of many essential substances found in plants and animals. Fortunately, humans do not use this process, which means any foreign pathogen in the human body that uses the MEP pathway can be targeted due to the different enzymes it puts to use.

SUMMARY

Materials and methods to design and create different analogs of oxdihydropyrimidine carboxylic acid, 4-(1H-imidazol-1-yl)phenol and 4-(1H-imidazol-5-yl)phenol that inhibit the 2-C-methyl-D-erythritol-2,4-cyclodiphosphate (MECDP) synthase, or IspF, enzymes of the MEP pathway, are described. In completing these objectives, the use of docking software (SYBYL) was used for the theoretical design of compounds.

Compounds were designed to inhibit the enzyme IspF present in the MEP pathway. The MEP pathway is a non-mevalonate pathway or 2-C-methyl-D-erythritol 4-phosphate/1-deoxy-D-xylulose 5-phosphate pathway (MEP/DOXP pathway) of isoprenoid biosynthesis. Analogs from the claimed chemical series were found to inhibit the enzyme IspF from *Burkholderia pseudomallei* using SPR and NMR assays at micromolar concentrations. Selected compounds were shown to have anti-bacterial activity in *Burkholderia thailandensis*, a non-fermenting motile gram-negative bacteria that is often used as a model for *Burkholderia pseudomallei*, a BSL-3 pathogen. *Burkholderia pseudomallei* is a class B pathogen and is considered a biosecurity threat. Selected analogs were screened against *Burkolderia pseudomallei* and found to have anti-bacterial activity.

Anti-infective 2-amino-1,6-dihydro-6-oxo-5-pyrimidinecarboxylic acid derivatives are disclosed. The anti-infective 2-amino-1,6-dihydro-6-oxo-5-pyrimidinecarboxylic acid derivatives are administered to a subject, such as a mammal, such as a human or a horse, to treat a bacterial infection. Compounds and compositions as disclosed herein are administered to a subject to inhibit bacterial growth, such as

*Burkholderia* spp. or *Mycobacterium* spp., and to treat subjects infected by such bacteria. The compounds disclosed in this application inhibit the enzymes IspD and or IspF and will be useful for the treatment of microbial infections. Compounds in this application have demonstrated anti-bacterial activity against *Burkholderia psuedomallei, Burkholderia thailandenesis* and *Plasmodium falciparum.*

Embodiments include compounds of Formula I:

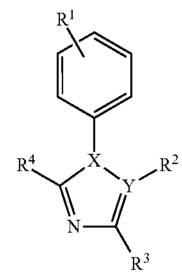

I wherein

X is N and Y is C, or X is C and Y is N;

$R^1$ is OH or $OR^5$, wherein $R^5$ is lower alkyl, acyl, $CH_2OCOCH_3$, or a prodrug;

$R^2$ is alkyl, aryl, alkylaryl, arylheteroaryl, or heteroaryl;

$R^3$ is H or lower alkyl; and $R^4$ is H or lower alkyl.

Embodiments include compounds of Formula II:

II wherein $R^1$ is H or lower alkyl;

$R^2$ is H or lower alkyl; and $R^3$ is alkyl, aryl, alkylaryl, arylheteroaryl, or heteroaryl.

Embodiments include compounds of Formula III:

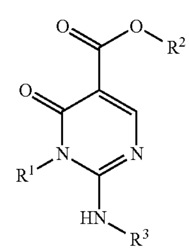

III wherein $R^1$ is H or lower alkyl;

$R^2$ is H or lower alkyl; and $R^3$ is alkyl, aryl, alkylaryl, arylheteroaryl, or heteroaryl.

The most potent anti-bacterial compound, against *Burkholderia* in initial tests was HGN-0118 from the pyrimidine series with 94.5% inhibition at 1 mM.

The most potent antimalarial compound in initial tests was HGN-0049, submicromolar for all three strains of drug resistant malaria. Another potent compound was HGN-0051.

Another potent antibacterial compound against *Burkholderia* is from the imidazole series, HGN-0095 with 88.3% inhibition.

BRIEF DESCRIPTION OF THE DRAWINGS

FIG. 1 shows a graph depicting *B. pseudomallei* growth rates (as measured by absorbance at $OD_{600}$) over time (min) in the presence of IspF inhibitor compounds HGN-0005, -0013, -0015, -0017, -0020, -0023, -0024, -0025, -0026, -0027, -0028, -0029, -0030, -0031, and -0032, and a negative control of no inhibitor.

FIG. 2 shows a graph depicting *B. pseudomallei* growth rates (as measured by absorbance at $OD_{600}$)) over time (min) in the presence of IspF inhibitor compounds HGN-0023, -0027, -0028, and -0029.

FIG. 3 shows a graph depicting *B. pseudomallei* growth rates (as measured by absorbance at $OD_{600}$) over time (min) in the presence of the IspF inhibitor compound HGN-0023 at concentrations of 1 mM, 500 μM, 250 μM, 125 and 62.5 μM; Controls included (a) DMSO and medium without bacteria (the blank); (b) DMSO, and (c) 300 μg/ml of kanamycin.

FIG. 4 shows a graph depicting *B. pseudomallei* growth rates (as measured by absorbance at $OD_{600}$) over time (min) in the presence of the IspF inhibitor compound HGN-0027 at concentrations of 1 mM, 500 μM, 250 μM, 125 μM, and 62.5 μM. Controls included (a) DMSO and medium without bacteria (the blank); (b) DMSO, and c) 300 μg/ml of kanamycin.

FIG. 5 shows a graph depicting *B. pseudomallei* growth rates (as measured by absorbance at $OD_{600}$) over time (min) in the presence of the IspF inhibitor compound HGN-0028 at concentrations of 1 mM, 500 μM, 250 μM, 125 μM, and 62.5 μM. Controls included (a) DMSO and medium without bacteria (the blank); (b) DMSO, and (c) 300 μg/ml of kanamycin.

FIG. 6 shows a graph depicting *B. pseudomallei* growth rates (as measured by absorbance at $OD_{600}$) over time (min) in the presence of the IspF inhibitor compound HGN-0029 at concentrations of 1 mM, 500 μM, 250 μM, 125 μM, and 62.5 μM. Controls included (a) DMSO and medium without bacteria (the blank); (b) DMSO, and (c) 300 μg/ml of kanamycin.

FIG. 7 shows a graph depicting *B. pseudomallei* strain 1026b growth rates (as measured by absorbance at $OD_{600}$) over time (min) in the presence of the IspF inhibitor compound HGN-0027 at concentrations of 1 mM, 500 μM, 250 μM, 125 μM, 62.5 μM, and 31.25 μM. Controls included (a) DMSO and medium without bacteria (the blank); (b) DMSO, and (c) 300 μg/ml of kanamycin.

FIG. 8 shows a graph depicting *B. pseudomallei* strain 340 growth rates (as measured by absorbance at $OD_{600}$) over time (min) in the presence of the IspF inhibitor compound HGN-0027 at concentrations of 1 mM, 500 μM, 250 μM, 125 μM, 62.5 μM, and 31.25 μM. Controls included (a) DMSO and medium without bacteria (the blank); (b) DMSO, and (c) 300 μg/ml of kanamycin.

FIG. 9 shows a graph depicting *B. pseudomallei* strain 1026b growth rates (as measured by absorbance at $OD_{600}$) over time (min) in the presence of the IspF inhibitor compound HGN-0028 at concentrations of 1 mM, 500 μM, 250 μM, 125 μM, 62.5 μM, and 31.25 μM. Controls included (a) DMSO and medium without bacteria (the blank); (b) DMSO, and (c) 300 μg/ml of kanamycin.

FIG. 10 shows a graph depicting *B. pseudomallei* strain 340 growth rates (as measured by absorbance at $OD_{600}$) over time (min) in the presence of the IspF inhibitor compound HGN-0028 at concentrations of 1 mM, 500 μM, 250 μM, 125 μM, 62.5 μM, and 31.25 μM. Controls included (a) DMSO and medium without bacteria (the blank); (b) DMSO, and (c) 300 μg/ml of kanamycin.

FIG. 11 shows a schematic of isoprenoid metabolism through the non-mevalonate pathway. The non-mevalonate pathway is the exclusive route to isoprenoid biosynthesis in eubacteria and the malaria parasite, *P. falciparum*. This pathway generates the basic isoprenoid building blocks IPP and DMAPP, which are elaborated to create diverse downstream products. Enzyme names are in bold.

DETAILED DESCRIPTION

Antimicrobial drug resistance is an urgent problem in the control and treatment of many of the world's most serious infections, including *Plasmodium falciparum* malaria, tuberculosis, and healthcare associated infections with Gram-negative bacteria. Because the nonmevalonate pathway of isoprenoid biosynthesis is essential in eubacteria and *P. falciparum* and this pathway is not present in humans, there is great interest in targeting the enzymes of non-mevalonate metabolism for antibacterial and antiparasitic drug development.

Isoprenoids include a large, diverse group of intracellular metabolites with multiple cellular functions, including roles in membrane structure, cellular respiration, and cell signaling [Zhang et al. (2011); Gershenzon and Dudareva (2007)]. There are two distinct biosynthetic routes for producing isopentenyl diphosphate (IPP) and dimethylallyl diphosphate (DMAPP), the basic isoprenoid building blocks. Mammals, including humans, exclusively utilize the classic metabolic route through mevalonate. In contrast, eubacteria, cyanobacteria, and plant chloroplasts use an alternative route that produces the key intermediate 1-D-deoxyxylulose 5-phosphate (DOXP) from pyruvate (FIG. 11) (Hunter, 2007). In bacteria that use this pathway, including *Escherichia coli, Burkholderia pseudomallei* and *Mycobacterium tuberculosis*, genetic studies have demonstrated that non-mevalonate isoprenoid biosynthesis is essential.

The malaria parasite *Plasmodium falciparum* annually kills nearly 1 million people, primarily young children. There is widespread resistance to older antimalarial drugs, such as chloroquine, and emerging resistance to new artemisinin-based therapies. *P. falciparum* also utilizes non-mevalonate isoprenoid biosynthesis, which is essential to the parasite. Novel non-mevalonate pathway inhibitors therefore hold great promise as antimicrobial agents with broad activity against major human pathogens, including *P. falciparum, B. pseudomallei, M tuberculosis*, and enterobacteria, for which global drug resistance has created an urgent need.

Compounds

The development of multi-drug resistance in bacteria and parasites that cause human disease is a growing problem in world health. The claimed compounds inhibit a unique enzyme pathway that is only found in certain types of infectious disease agents, but not in human beings. Compounds from this series will lead to improved drugs and other treatments for infectious diseases such as malaria and a range of bacterial infections. Members have shown antibacterial activity against *Burkholderia thailandensis*.

Figure 1:
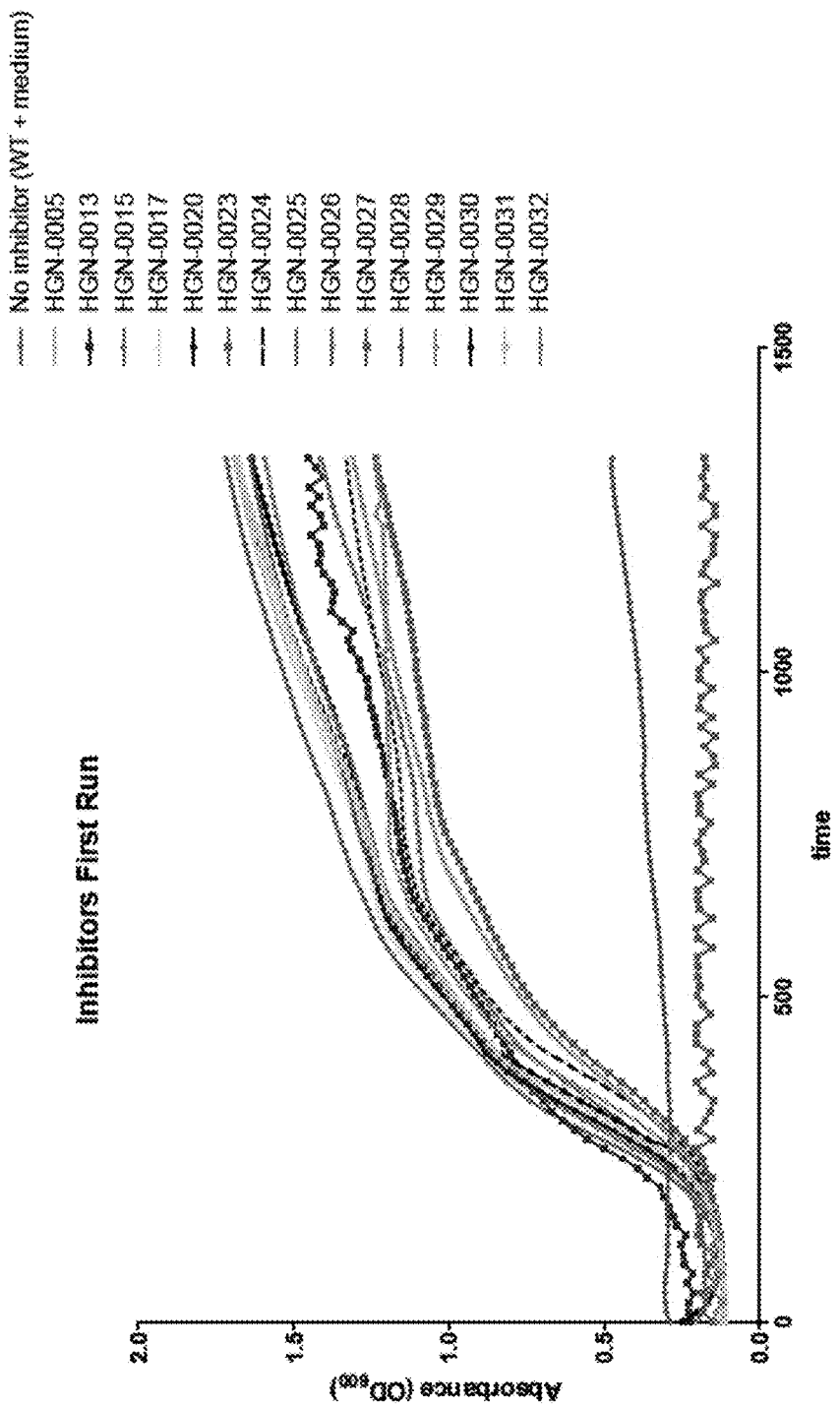
Figure 2:
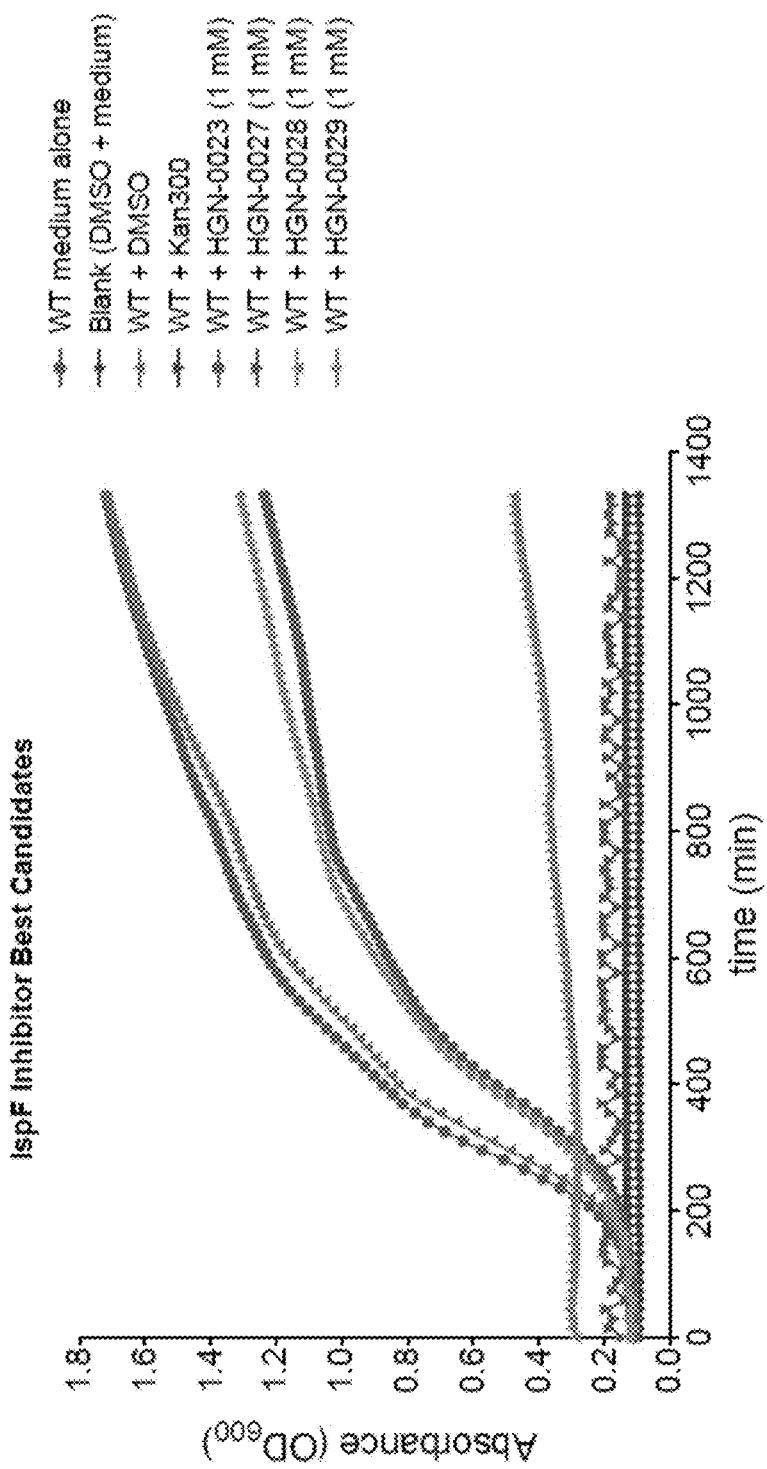
Figure 3:
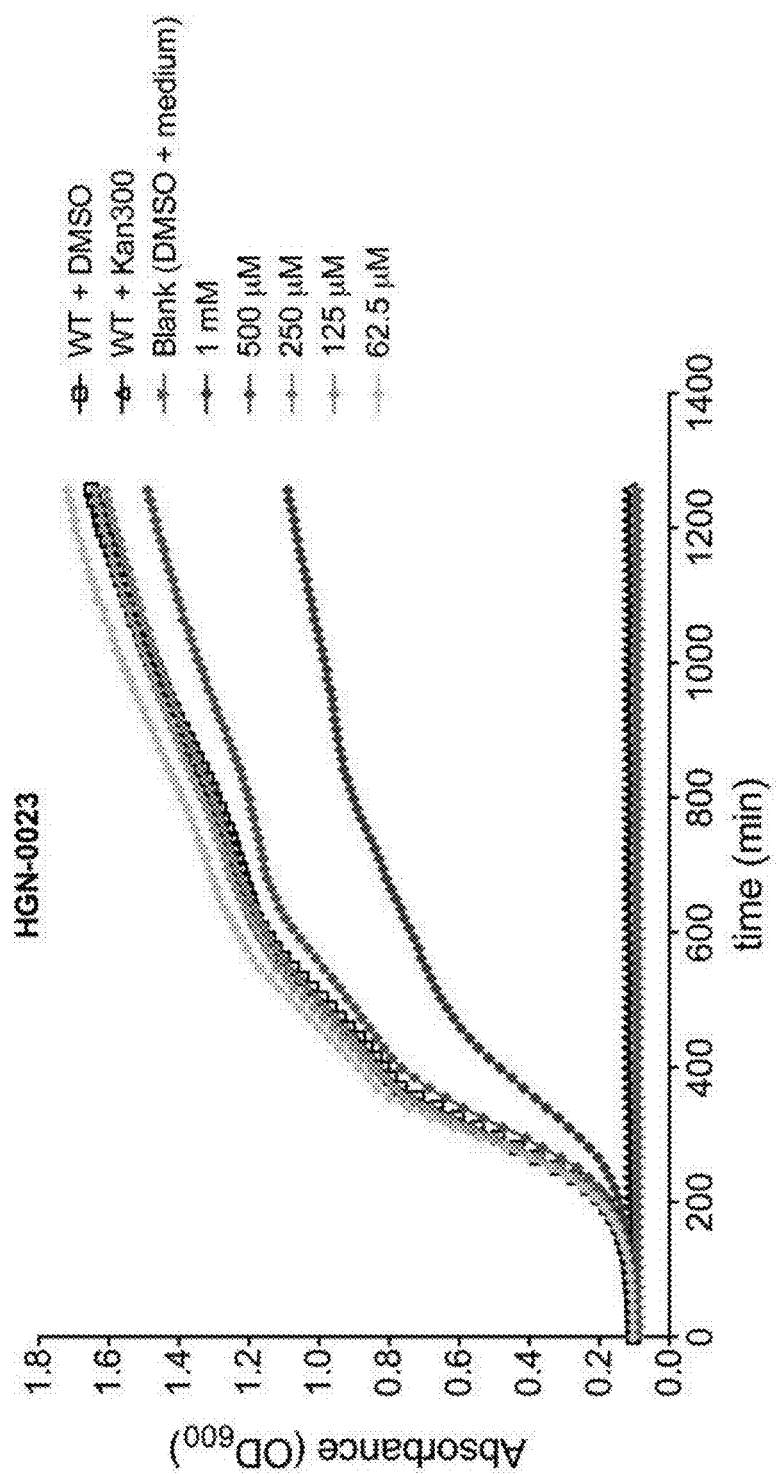
Figure 4:
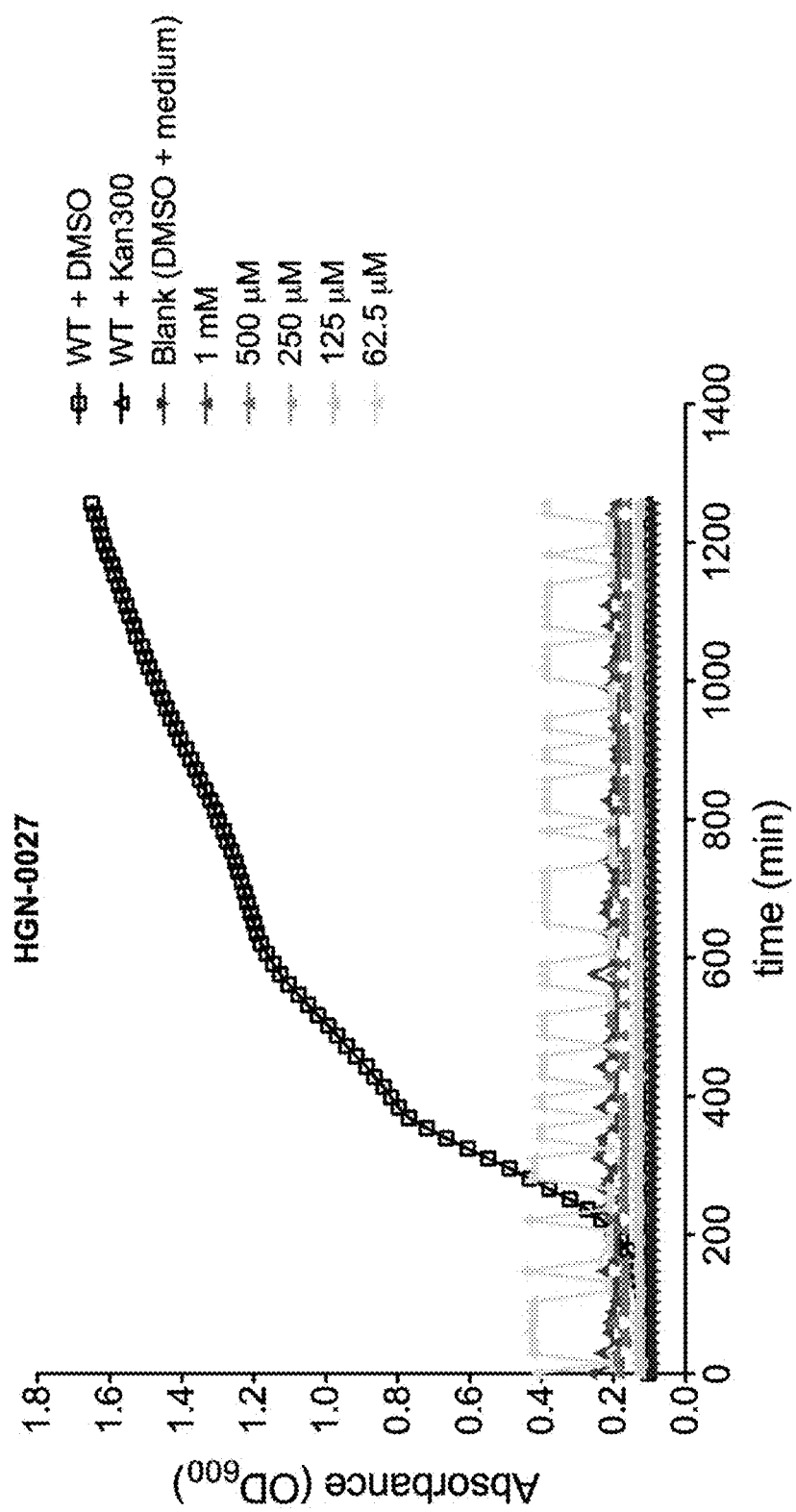
Figure 5:
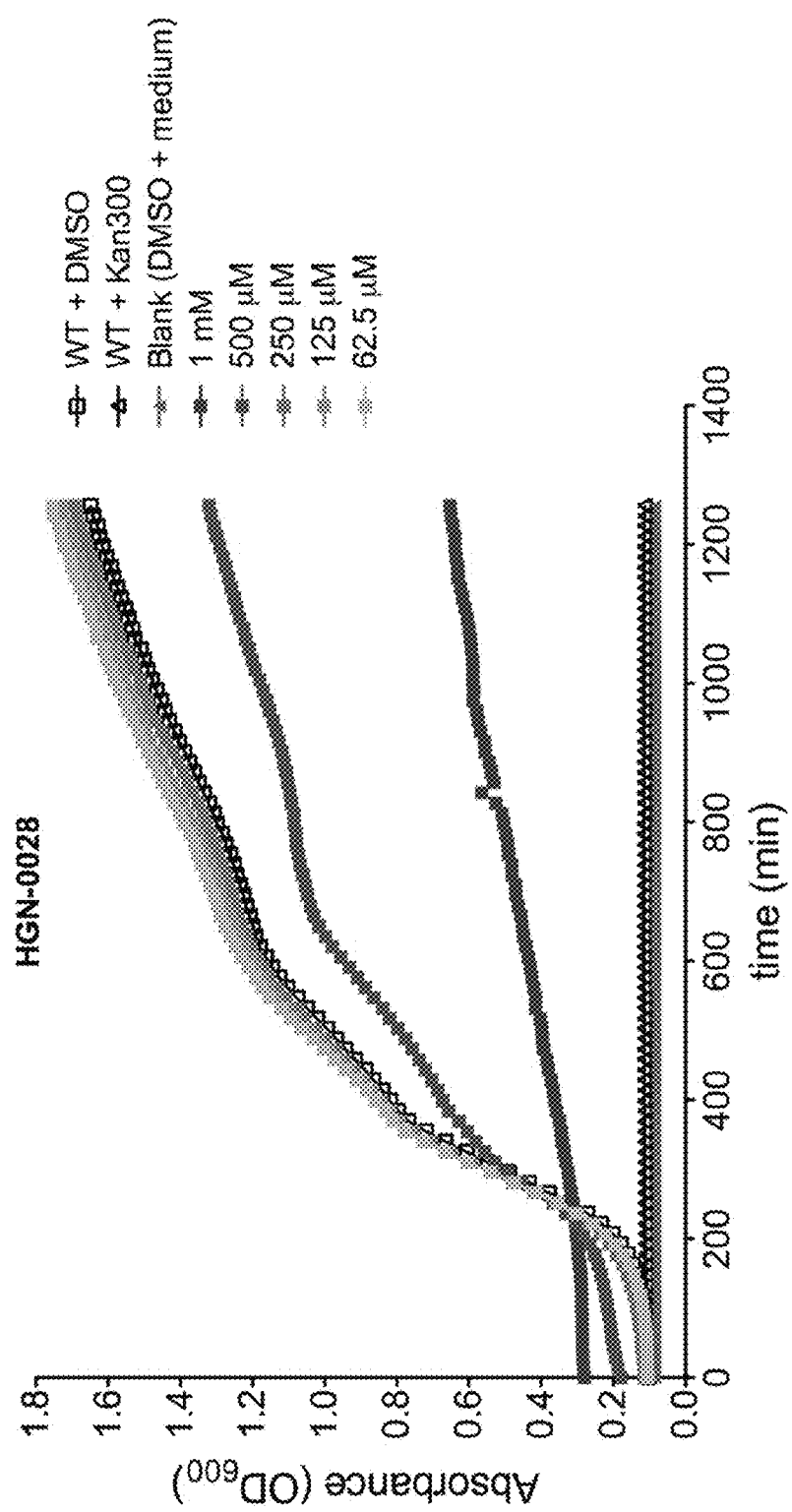
Figure 6:
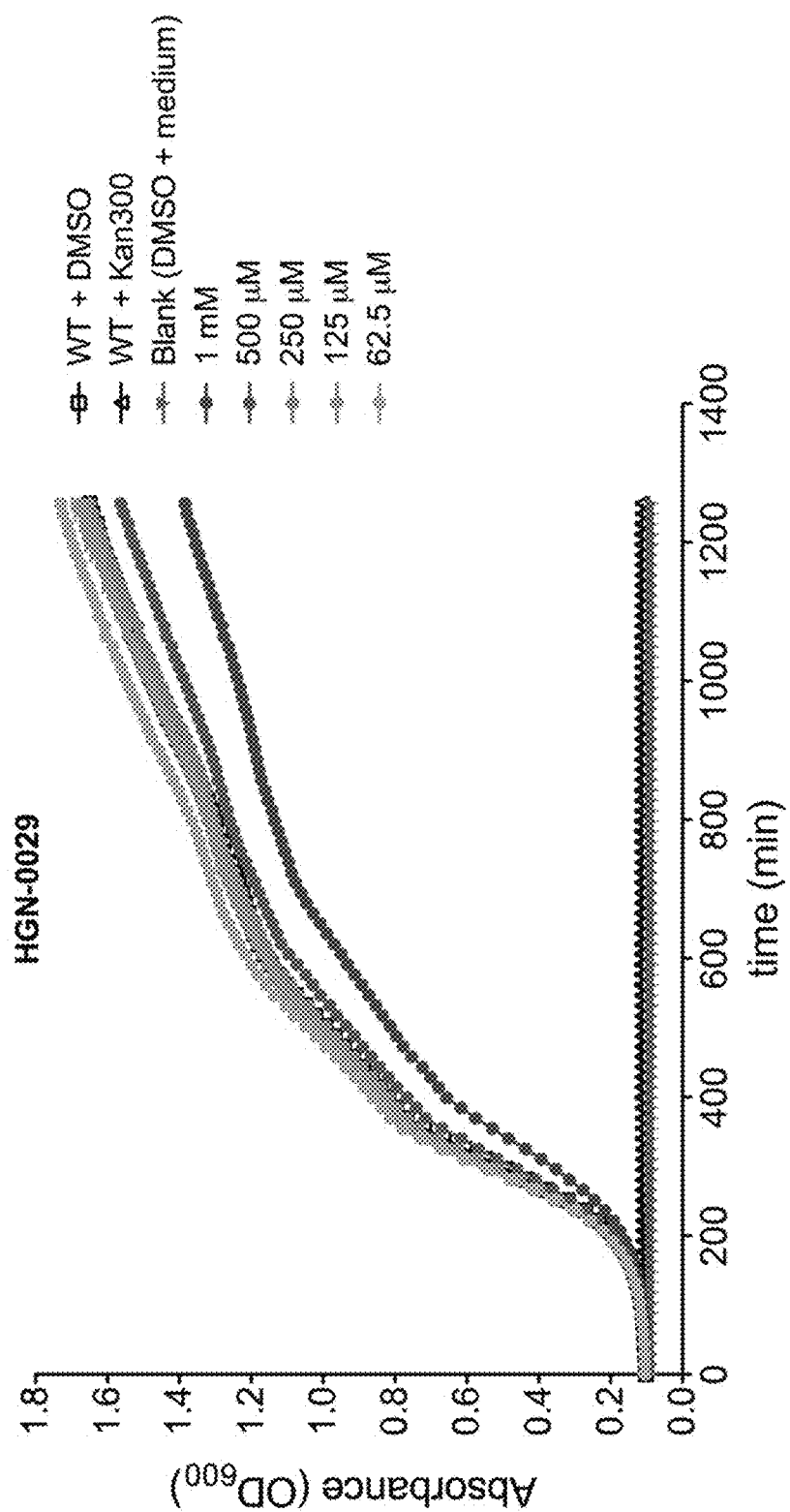
Figure 7:
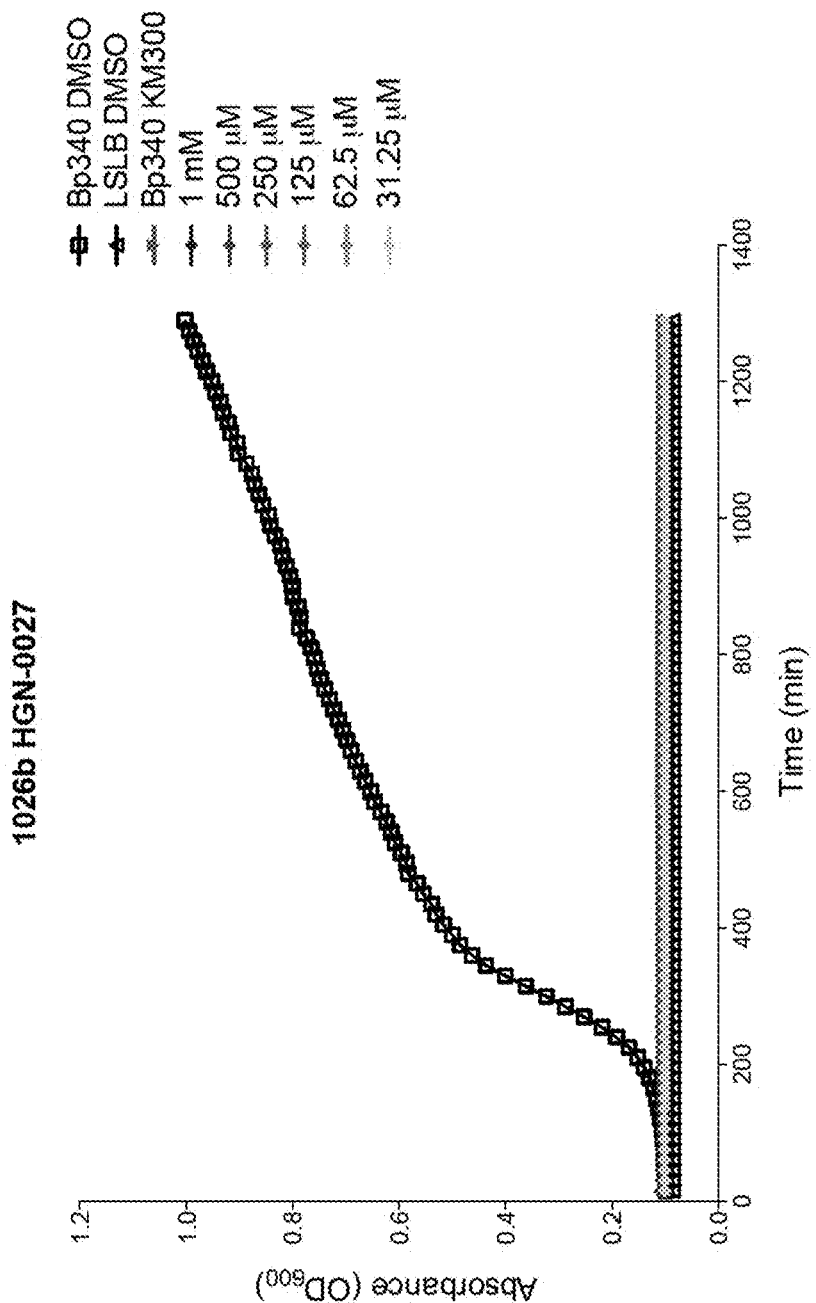
Figure 8:
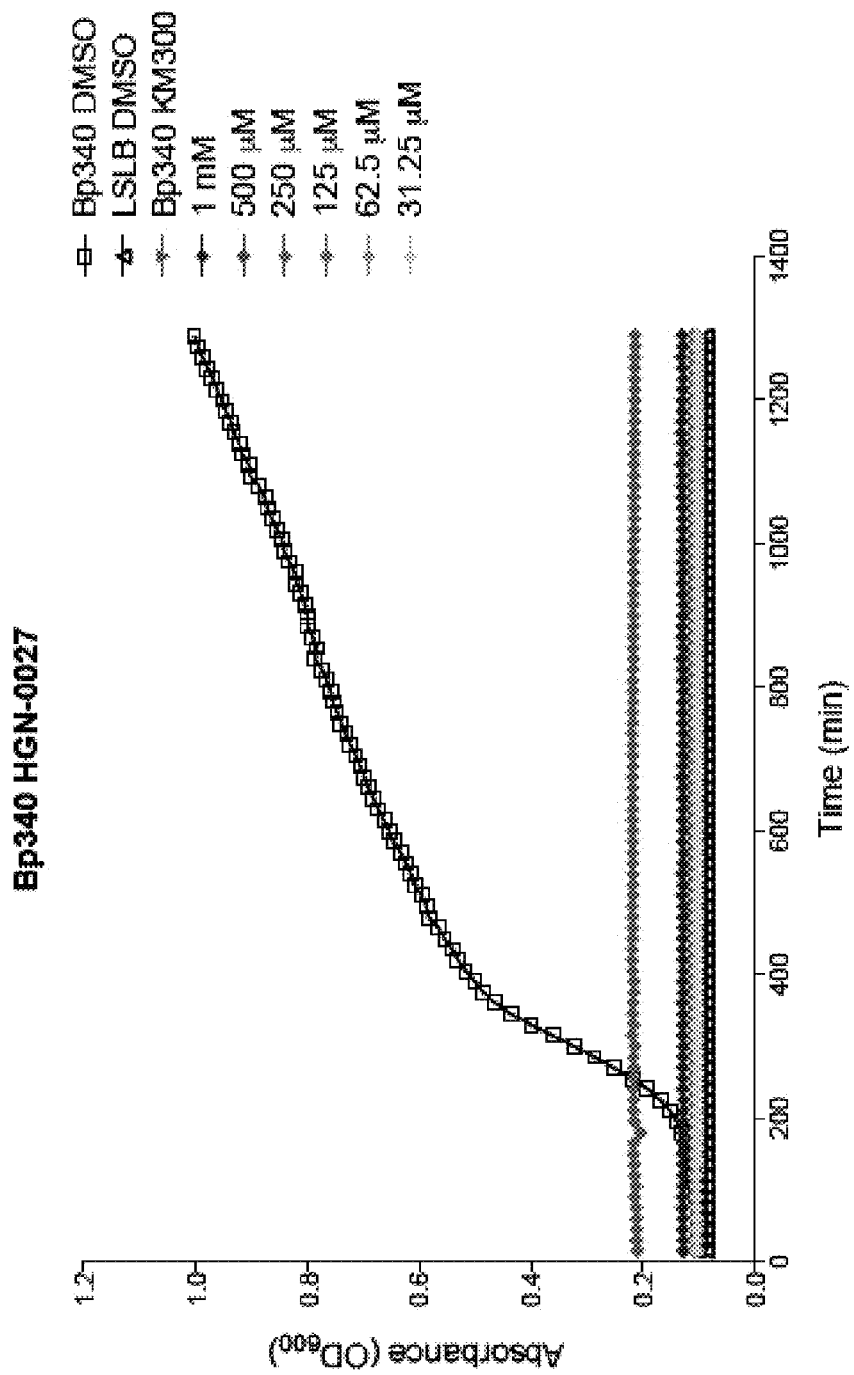
Figure 9:
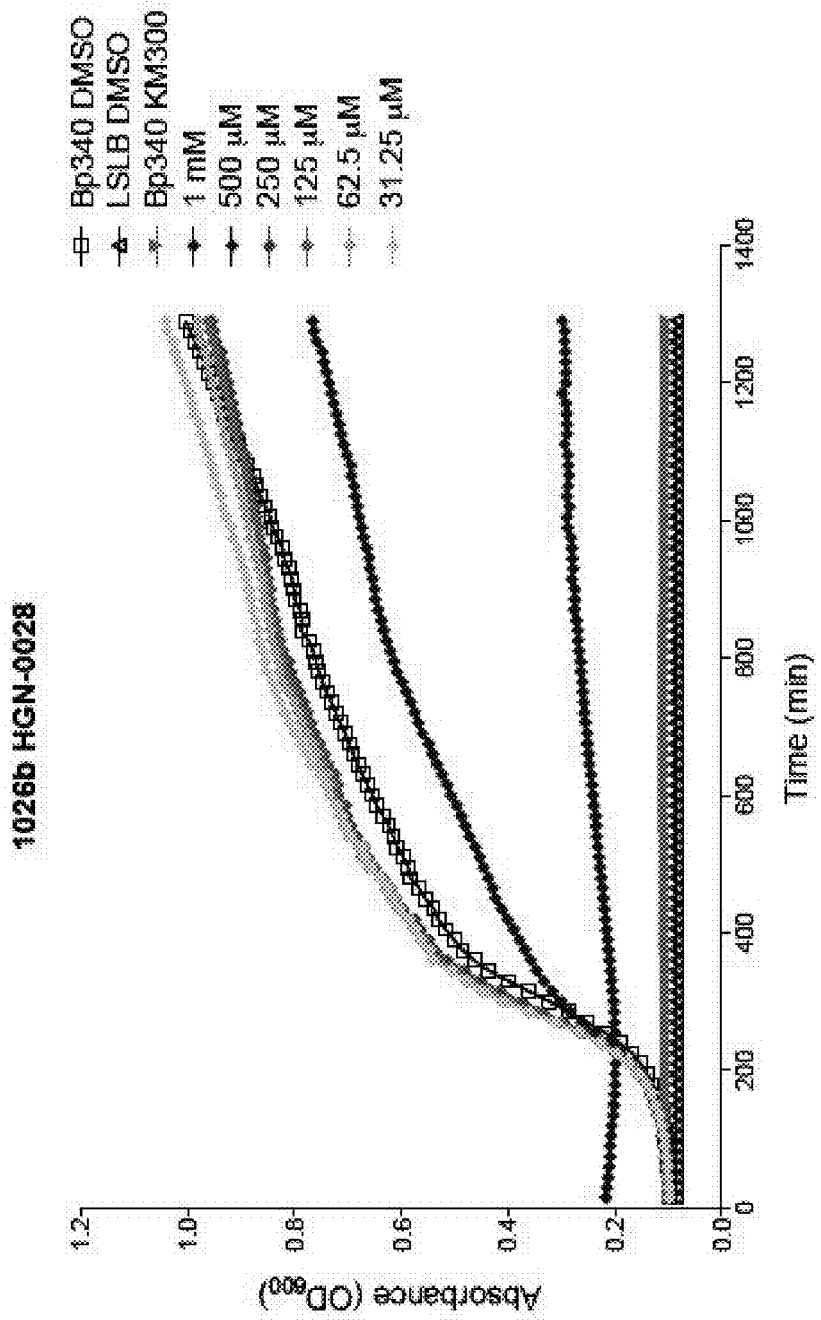
Figure 10:
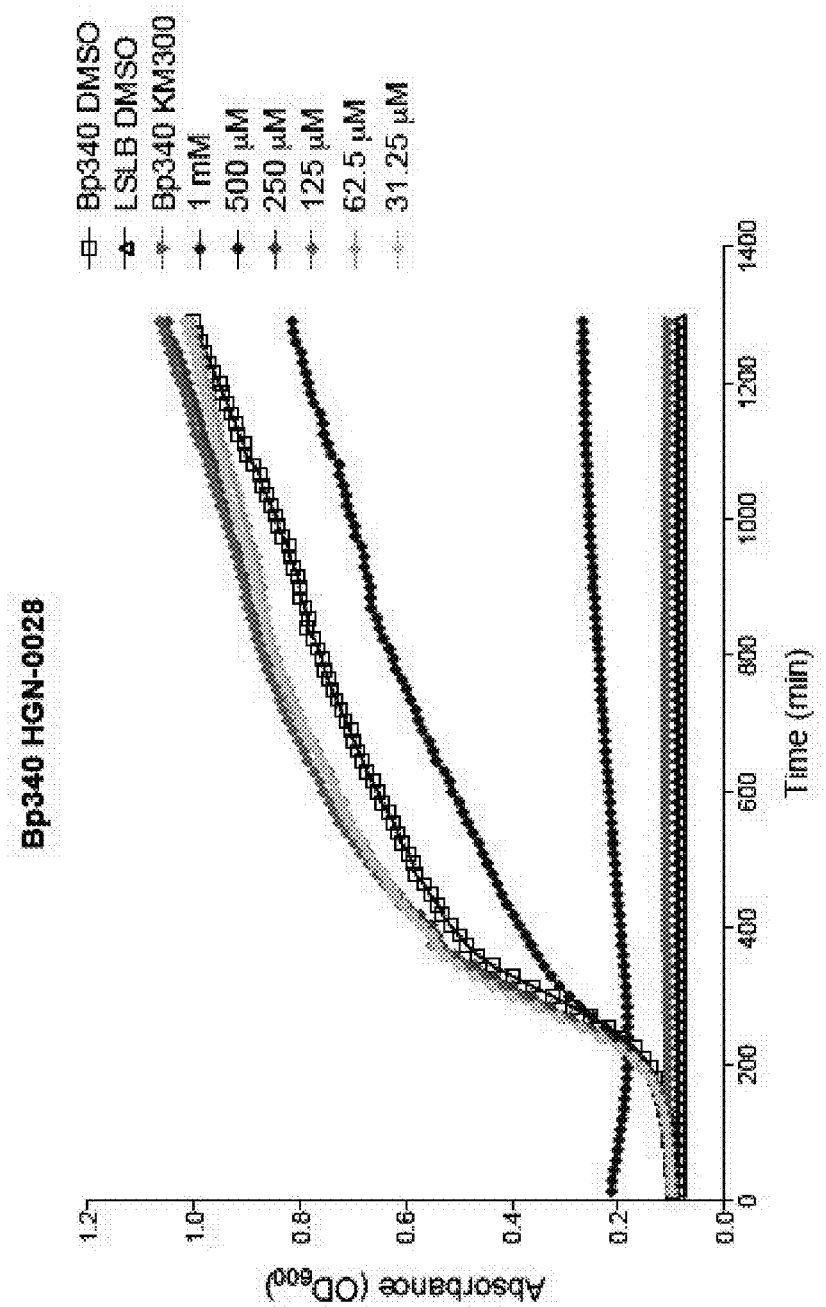
Figure 11:
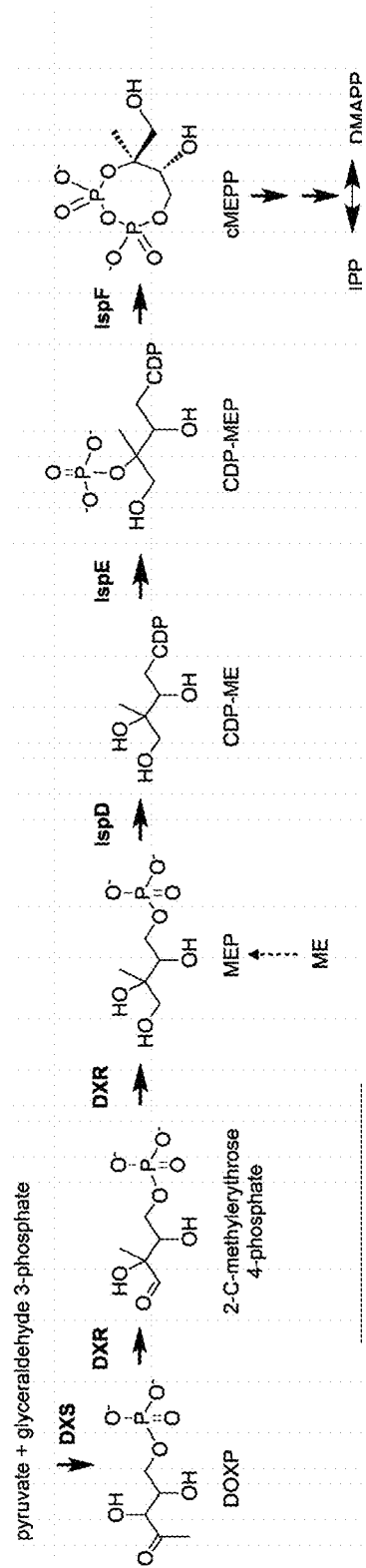

Materials and methods to design and create different analogs of oxdihydropyrimidine carboxylic acid that inhibit the IspF enzymes of the MEP pathway are described. Embodiments include substituted pyrimidine and imidazole derivatives, compositions containing the pyrimidine and imidazole derivatives, and methods of treatment using therapeutically effective amounts of the pyrimidine and imidazole derivatives. Compounds and compositions disclosed herein can be used to treat bacterial disease, wherein the bacteria utilitze the non-mevalonate pathway, such as *Burkholderia* spp. and *Mycobacterium* spp.

Embodiments include compounds of Formula I:

I wherein

X is N and Y is C, or X is C and Y is N;

$R^1$ is OH or $OR^5$, wherein $R^5$ is lower alkyl, acyl, $CH_2OCOCH_3$, or prodrugs for phenolic groups;

$R^2$ is alkyl, aryl, alkylaryl, arylheteroaryl, or heteroaryl;

$R^3$ is H or lower alkyl; and $R^4$ is H or lower alkyl.

Embodiments include compounds of Formula II:

II wherein $R^1$ is H or lower alkyl;

$R^2$ is H or lower alkyl; and $R^3$ is alkyl, aryl, alkylaryl, arylheteroaryl, or heteroaryl.

Embodiments also include compounds of Formula III:

III 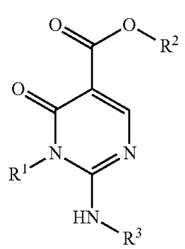 wherein $R^1$ is H or lower alkyl;

$R^2$ is H or lower alkyl; and $R^3$ is alkyl, aryl, alkylaryl, arylheteroaryl, or heteroaryl Anti-infective 2-amino-1,6-dihydro-6-oxo-5-pyrimidinecarboxylic acid derivatives are disclosed.

Specific compounds are disclosed in Tables 2-5 of Example 37 and Tables 6-9 of Example 38 herein.

Pharmaceutical Compositions

Although it is possible for compounds to be administered alone in a unit dosage form, compounds are typically administered in admixture with a carrier as a pharmaceutical composition to provide a unit dosage form. A pharmaceutical composition comprises a pharmaceutically acceptable carrier in combination with a compound disclosed herein or a pharmaceutically acceptable salt thereof.

A pharmaceutically acceptable carrier includes, but is not limited to, physiological saline, ringers, phosphate-buffered saline, and other carriers known in the art. Pharmaceutical compositions can also include additives such as, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier in combination with a therapeutic compound or a pharmaceutically acceptable acid addition salt of a compound are known to those of skill in the art. The invention also includes pharmaceutically acceptable salts of the compounds of the invention. The compounds of the invention are capable of forming both pharmaceutically acceptable acid addition and/or base salts.

All methods can include the step of bringing one of the compounds disclosed herein in association with a carrier and one or more additives. Formulations generally are prepared by uniformly and intimately bringing a compound into association with a liquid carrier or a finely divided solid carrier or both, and then, if necessary, shaping the product into the desired unit dosage forms.

As used herein, the term "pharmaceutically acceptable carrier" means a non-toxic, inert solid, semi-solid or liquid filler, diluent, encapsulating material or formulation auxiliary of any type.

Liquid dosage forms for oral administration include pharmaceutically acceptable emulsions, microemulsions, solutions, suspensions, syrups and elixirs.

Injectable preparations, for example, sterile injectable aqueous or oleaginous suspensions may be formulated according to the known art using suitable dispersing or wetting agents and suspending agents.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate; e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches.

Compositions may also be formulated for delivery as a liquid aerosol or inhalable dry powder.

The compounds may also be formulated for use as topical powders and sprays that can contain, in addition to the compounds of this invention, excipients such as lactose, talc, silicic acid, aluminum hydroxide, calcium silicates and polyamide powder, or mixtures of these substances.

Transdermal patches have the added advantage of providing controlled delivery of a compound to the body.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial or parasitic infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder, the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

A "kit" used in the instant application can include a container comprising the pharmaceutical compositions and may also include divided containers such as a divided bottle or a divided foil packet. The container can be in any conventional shape or form as known in the art that is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box.

A "daily dose" can be a single tablet or capsule or several tablets or capsules to be taken on a given day.

The kits of the present invention may also include, in addition to ISPF inhibitors, one or more additional pharmaceutically active compounds. Preferably, the additional compound is another ISPF inhibitor or another compound useful to treat bacterial or parasitic infections. The additional compounds may be administered in the same dosage form as the ISPF inhibitor compound or in different dosage forms. Likewise, the additional compounds can be administered at the same time as the ISPF inhibitor compound(s) or at different times.

Methods of Treatment

*Burkholderia* spp. cause a number of diseases. For instance, *Burkholderia mallei* is the etiologic agent of glanders. While glanders primarily affects horses, humans, dogs, cats, goats, mules, and donkeys can also contract glanders. Glanders often manifests itself as pulmonary infection. In pulmonary infections, pneumonia, pulmonary abscesses, and pleural effusion can occur. Glanders can also be a localized infection of open wounds and of mucus membranes in the eyes, nose, and respiratory tract. *Burkholderia thailandensis* is an opportunistic pathogen that can cause pneumonia and septicemia. *Burkholderia pseudomallei* the causative agent of melioidosis.

In an embodiment, a compound or composition disclosed herein can be administered to a subject to treat a *Burkholderia* infection. In an embodiment, compounds and compositions disclosed herein can be administered to a subject to treat glanders. An embodiment includes administering a compound or composition disclosed herein to a subject concurrently with the administration of at least one of tetracycline, ciprofloxacin, streptomycin, novobiocin, gentamicin, imipenem, ceftrazidime, or a sulfonamide. In another embodiment, compounds and compositions disclosed herein can be administered to a subject to treat melioidosis.

Multidrug resistant tuberculosis (MDR-TB), and even extensively drug resistant tuberculosis (XDR-TB) has become more prevalent in the last 20 to 40 years. New treatments are sought to battle the rising rates of drug resistant TB cases. *Mycobacterium tuberculosis*, the etiologic agent of tuberculosis, generates isopentenyl pyrophosphate (IPP) and dimethylallyl pyrophosphate (DMAPP) via the non-mevalonate pathway. Thus, *M. tuberculosis* is a target for the compounds and compositions disclosed herein. Treatment with compounds and compositions as disclosed herein represent new treatments for tuberculosis. As such, an embodiment includes administering a compound or composition as disclosed herein to a subject with tuberculosis. The treatment with the compounds and compositions disclosed herein may optionally be administered with at least one of the first line drugs ethambutol, isoniazid, rifampicin, or pyrazinamide. The treatment with the compounds and compositions disclosed herein may optionally be administered with at least one of the second line drugs an aminoglycoside (e.g., streptomycin, kanamycin, amikacin), a fluoroquinolone (e.g., ciprofloxacin, ofloxacin, sparfloxacin, moxifloxacin, etc.), capreomycin, viomycin, enviomycin, a thioamide (e.g., ethionamide and protionamide), cycloserine, para-aminosalicylic acid, thiacetazone, clofazimine, linezolid, a macrolide (e.g., clarithromycin, azithromycin), or amoxicillin/clavulanate.

Methods of treating bacterial or parasitic infection include administering a compound or composition as described herein, and optionally further comprising administering at least one other antibacterial agent.

Definitions

The term "compound disclosed herein" and similar terms refers to an IspF inhibitor compound as described herein, a compound of formulae I, II, or III or compounds of Tables 2-9, or a compound described in the Examples, or a pharmaceutically acceptable salt, solvate, clathrate, hydrate, polymorph or prodrug thereof.

Compounds disclosed herein may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

The term "alkyl" refers to a saturated linear or branched hydrocarbon radical. In one embodiment, alkyl has from 1 to 8 carbon atoms. In another embodiment, alkyl has from 1 to 6 carbon atoms. In another embodiment, alkyl has from 1 to 4 carbon atoms. In one embodiment, alkyl has 1 carbon. The alkyl group may optionally be substituted with one or more substituents such as fluorine, chlorine, alkoxy groups having from 1 to 8 carbon atoms (e.g., methoxy or ethoxy), or amido groups having from 1 to 8 carbon atoms, such as acetamido. These substituents may themselves be substituted with one or more functional groups such as hydroxy groups, carboxy groups, acetoxy groups, or halogens.

As used herein "aryl" means a mono- or poly-nuclear aromatic hydrocarbon radical. Examples of "aryl" groups include, but are not limited to aromatic hydrocarbons such as a phenyl group or a naphthyl group. The aromatic group may optionally be substituted with one or more substituents such as fluorine, chlorine, alkyl groups having from 1 to 8 carbon atoms (e.g., methyl or ethyl), alkoxy groups having from 1 to 8 carbon atoms (e.g., methoxy or ethoxy), alkoxyalkyl groups having from 1 to 8 carbon atoms and one or more oxygen atoms, or amido groups having from 1 to 8 carbon atoms, such as acetamido. These substituents may themselves be substituted with one or more functional groups such as hydroxy groups, carboxy groups, acetoxy groups, or halogens.

In one embodiment, aryl is a phenyl group or a naphthyl group that is either unsubstituted or substituted.

In another embodiment, aryl is a heteroaryl in which one or more of the carbon atoms of an aromatic hydrocarbon is substituted with a nitrogen, sulfur, or oxygen. Examples of a "heteroaryl" include, but are not limited to pyridine, pyrimidine, pyran, dioxin, oxazine, and oxathiazine. Likewise, the heteroaryl may optionally be substituted with functional groups such as hydroxy groups, carboxy groups, halogens, and amino groups.

The term "lower" refers to a group having up to four atoms. For example, a "lower alkyl" refers to an alkyl radical having from 1 to 4 carbon atoms, "lower alkoxy" refers to "—O—($C_1$-$C_4$)alkyl. Included in this definition is a lower group having 1 to 3 carbon atoms.

The term "cycloalkyl" refers to a saturated, mono- or polycyclic alkyl radical having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, -cyclodecyl, octahydro-pentalenyl, and the like. Cycloalkyl groups may be optionally substituted with one or more substituents.

As used herein, the term "haloalkyl" means an alkyl group, in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "polymorph" refers to solid crystalline forms of a compound or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "substituent" refers to a group "substituted" on an alkyl, cycloalkyl, aryl, heterocyclyl, or heteroaryl group at any atom of that group. Suitable substituents include, without limitation, alkyl, alkenyl, alkynyl, alkoxy, halo, hydroxy, cyano, nitro, amino, $SO_3H$, perfluoroalkyl, perfluoroalkoxy, methylenedioxy, ethylenedioxy, carboxyl, oxo, thioxo, imino (alkyl, aryl, aralkyl), S(O)nalkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The term "antibacterial" refers to compounds or compositions disclosed herein that have either bactericidal or bacteriostatic activity. An "antibacterial" compound or composition in this context can inhibit the growth of *B. mallei, B. pseudomallei*, and other *Burkholderia* spp., and other gram-negative bacteria. Additionally, an antibacterial compound or composition in this context can inhibit the growth of *Mycobacterium tuberculosis* and other *Mycobacterium* spp. The term "inhibiting the growth" indicates that the rate of increase in the numbers of a population of particular bacteria is reduced. Thus, the term includes situations in which the bacterial population increases but at a reduced rate, as well as situations where the growth of the population is stopped, as well as situations where the numbers of the bacteria in the population are reduced or the population even eliminated.

An "antimicrobial agent" refers to a substance that kills microbes or inhibits microbial growth or replication. Microbes are microorganisms that include bacteria, fungi, or protozoans. An antimicrobial agent can be an antibiotic (e.g., streptomycin) or can be an non-pharmaceutical antimicrobial (e.g., chlorhexidine, silver, triclosan).

The terms "treat" and "treatment" refer to therapeutic treatment, wherein the object is to inhibit or slow down (lessen) an undesired physiological change or disorder, such as the development or spread of infection. For purposes of this invention, beneficial or desired clinical results include, but are not limited to, alleviation of symptoms, diminishment of extent of disease, stabilized (i.e., not worsening) state of disease, delay or slowing of disease progression, amelioration, or palliation of the disease state. "Treatment" can also mean prolonging survival as compared to expected survival if not receiving treatment. Those in need of treatment include those already with the condition or disorder as well as those prone to have the condition or disorder or those in which the condition or disorder is to be prevented.

"Mammal" for purposes of treatment or therapy refers to any animal classified as a mammal, including humans, domestic and farm animals, and zoo, sports, or pet animals, such as dogs, horses, cats, cows, and the like. Preferably, a mammal is human.

EXAMPLES

Example 1

Analyis of IspF

To design inhibitor compounds, IspF was analyzed to better designed compounds to inhibit its function.

IspF Screening by NMR Spectroscopy

To design IspF inhibitor compounds, the IspF protein was analyzed by nuclear magnetic resonance (NMR) spectroscopy. NMR samples were prepared by diluting tagless, concentrated BpIspF protein in SEC buffer to 20 μm (60 μm monomer) with NMR buffer (10 mM K-Phos (pH 7.8), 50 mM NaCl, 10% (v/v) $2H_2O$). Compounds were assayed at ligand concentrations of 400 μm, with 400 μm cytidine and 20 μM deuterated dimethyl sulfoxide (d6-DMSO) present in a 500 μM sample volume. All experiments were conducted on a 600-MHz Bruker AV spectrometer with TCI cryoprobe set to 280 K. Screening was done using ligand-observe, protonbased one-dimensional saturation transfer difference nuclear magnetic resonance (STD-NMR) (Mayer et al., 1999) and two-dimensional nuclear Overhauser effect spectroscopy (NOESY) according to (Begley et al, 2010).

Briefly, 32 scans and 32,000 points were acquired over a 14 ppm sweep width for STD-NMR data, with a total recycle delay of 4.0 s for each mixture. A low-power 30-ms spin-lock pulse was added to filter out low-level protein peaks, and a WATERGATE sequence added to suppress bulk water signal (Piotto et al., 1992). STD-NMR pre-saturation was done using a 3.0 s-long train of Gaussian-shaped pulses with a spectral width of 600 Hz focused at −1.0 ppm, with reference irradiation set to 30 ppm. For NOESY experiments, 2,048 9 160 points were collected with a mixing time of 500 ms and a recycle delay of 2.0 s, with WATERGATE solvent suppression for each mixture.

Sequence Analysis

The IspF from nine pathogens were aligned and studied for sequence conservation. The nine pathogens were *Escherichia coli, Yersinia pestis, Haemophilus influenzae, Burkholderia pseudomallei, Mycobacterium tuberculosis, Plasmodium vivax, Brucella melitensis, Babesia bovis*, and *Plasmodium falciparum* (IspF subunit from the bifunctional IspDF enzyme). Of note, D48 was 100% conserved in the 9 pathogens. This amino acid residue does not bind substrate and has a putative structural role and a putative functional role of assisting $Zn^{2+}$ ion position during catalysis. There was also 100% conservation in having the "DIG" motif, whereby D58 binds ribose and G60 is necessary for the conserved pseudo β-turn.

Additionally screening and substrate-derived fragments were soaked into crystals of IspF from *B. pseudomallei*. This allowed for screening ligand binding and conformation selection as analyzed by the drug design software AutoDocks (version 4.0) (The Scripps Research Institute, La Jolla, Calif.). Through this software, specific candidate compounds and classes of candidate compounds were selected.

Example 2

Synthesis of Sodium 2-((4-chlorophenethyl)amino-4-oxidopyrimidine-5-carboxylate (HGN-0028)

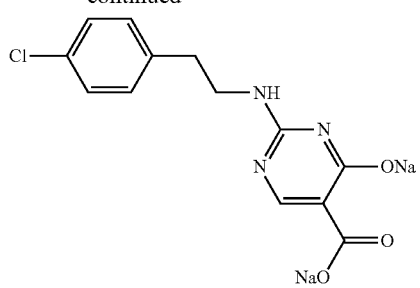

A mixture of ethyl 2-((4-chlorophenethyl)amino)-6-oxo-1,6-dihydropyrimidine-5-carboxylate (60 mg, 1.86 mmol) and sodium hydroxide (1M) was heated up to reflux for 4 hours and then cooled to 40° C. overnight. After heating, the solution was completely dissolved without precipitate and condensed. $^1$H-NMR confirmed the product as sodium 2-((4-chlorophenethyl)amino-4-oxidopyrimidine-5-carboxylate (HGN-0028) (59 mg, 94% yield).

Example 3

Synthesis of ethyl 6-oxo-2-(((tetrahydrofuran-2-yl)methyl)amino)-1,6-dihydropyrimidine-5-carboxylate (HGN-0017)

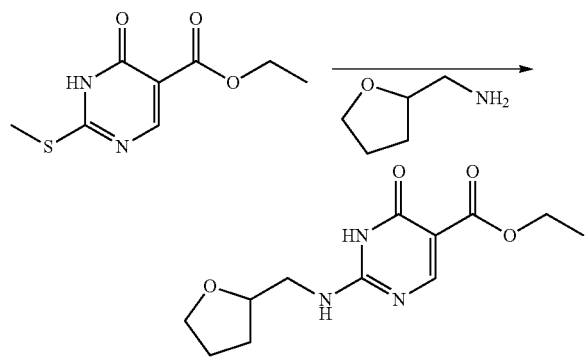

(tetrahydrofuran-2-yl)methanamine (142 mg, 1.40 mmol) was added into ethyl 2-(methylthio)-6-oxo-1,6-dihydropyrimidine-5-carboxylate (300 mg, 1.40 mmol) in methanol and refluxed overnight. After half of the starting material was consumed, the reaction mixture was reheated again overnight. Then the reaction mixture was cooled and the precipitate filtered. $^1$H-NMR confirmed the product as ethyl 6-oxo-2-(((tetrahydrofuran-2-yl)methyl)amino)-1,6-dihydropyrimidine-5-carboxylate (HGN-0017) (176 mg, 47% yield).

Example 4

Synthesis of ethyl 2-((1,1'-biphenyl)-4-ylamino)-6-oxo-1,6-dihydropyrimidine-5-carboxylate (HGN-0033)

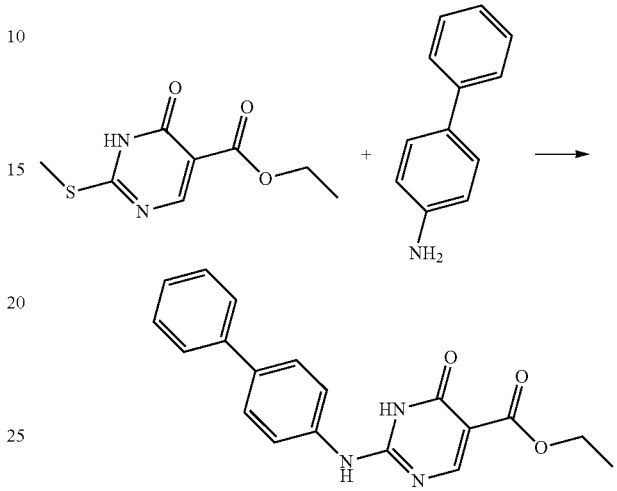

Ethyl 2-(methylthio)-6-oxo-1,6-dihydropyrimidine-5-carboxylate (60 mg, 0.233 mmol) was added to 1,1'-biphenyl-4-amine (79 mg, 0.467 mmol) dissolved in ethanol. The solution was heated in an oil bath to 80° C., while stirring, in reflux, for 72 hours. The sample was filtered and dried. $^1$H-NMR confirmed the structure (31 mg, 40% yield).

Example 5

Synthesis of ethyl 6-oxo-2-((4-(piperidin-1-yl)phenyl)amino)-1,6-dihydropyrimidine-5-carboxylate (HGN-0034)

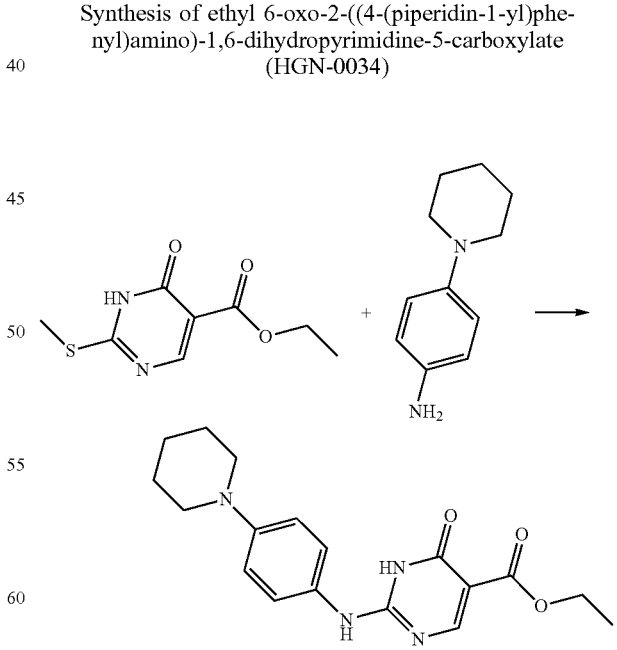

Ethyl 2-(methylthio)-6-oxo-1,6-dihydropyrimidine-5-carboxylate (200 mg, 0.934 mmol) was added to 4-(piperidin-1-yl)aniline (158 mg, 0.934 mmol) dissolved in ethanol. The solution was heated in an oil bath to 80° C., while stirring, in reflux, for 72 hours. The sample was filtered and dried. ¹H-NMR confirmed the product (HGN-0034) (15 mg, 0.447 mmol).

Example 6

Synthesis of 2-((1,1'-biphenyl)-4-ylamino)-6-oxo-1, 6-dihydropyrimidine-5-carboxylic acid (HGN-0035)

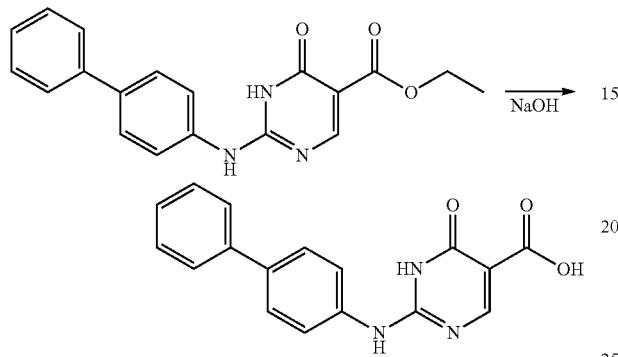

A mixture of ethyl 2-((1,1'-biphenyl)-4-ylamino)-6-oxo-1,6-dihydropyrimidine-5-carboxylate (100 mg, 0.298 mmol), sodium hydroxide (1M, aq), and methanol was stirred at 70° C. for 2 hours and for 40° C. overnight. The ester did not dissolve in 3 mL methanol. The ester was then put in 3 mL dioxane and heated to 103° C. for 4 hours with an additional 1 mL of NaOH added. The reaction mixture was then heated at 40° C. overnight. After the overnight heating, the reaction mixture was cooled and the solvent removed. The reaction mixture was diluted with water, and the pH was adjusted to about 3.0. The reaction mixture was filtered to obtain the end product. ¹H-NMR confirmed the product (55 mg, 60.0% yield).

Example 7

Synthesis of 6-oxo-2-((4-(piperidin-1-yl)phenyl) amino)-1,6-dihydropyrimidine-5-carboxylic acid

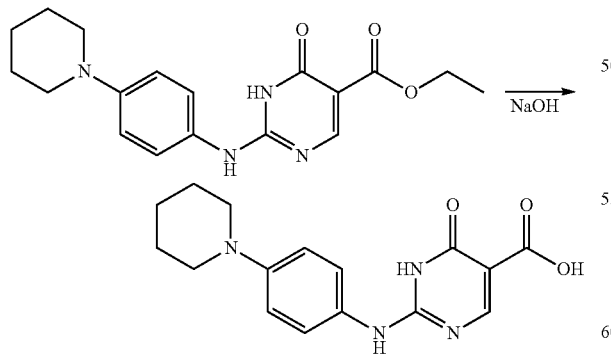

A mixture of ethyl 6-oxo-2-((4-(piperidin-1-yl)phenyl) amino)-1,6-dihydropyrimidine-5-carboxylate (100 mg, 0.298 mmol), sodium hydroxide (1M, aq), and methanol was stirred at 70° C. for 2 hours and for 40° C. overnight. The reaction mixture was filtered to remove the solid precipitate to verify product. Recombined the filtrate and precipitate to concentrate by adding 3 mL dioxane and heated to 103° C. for 4 hours with an additional 1 mL of NaOH added. The reaction mixture was then heated at 40° C. overnight. After the overnight heating, the reaction mixture was cooled and the solvent removed. The reaction mixture was diluted with water, and the pH was adjusted to about 3.0. The reaction mixture was filtered to obtain the end product. ¹H-NMR confirmed the product (55 mg, 60% yield).

Example 8

Synthesis of ethyl 2-((4-(morpholinophenylamino)-6-oxo-1,6-dihydropyrimidine-5-carboxylate (HGN-0037)

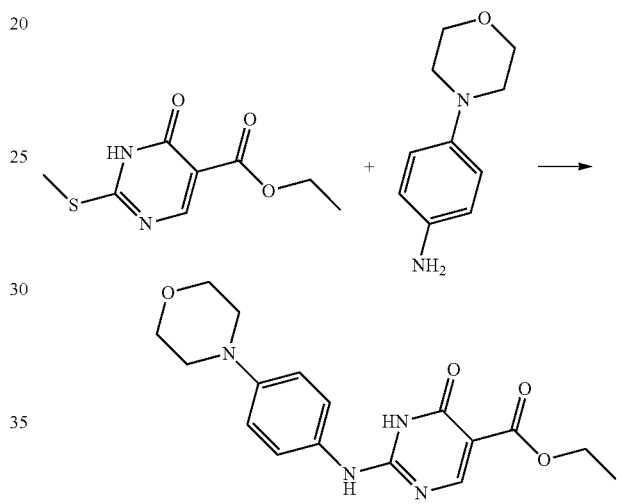

Ethyl 2-(methylthio)-6-oxo-1,6-dihyropyrimidine-5-carboxylate (311 mg, 1.452 mmol) and 4-morpholinoaniline (259 mg, 1.452 mmol) were dissolved in 10 mL of ethanol and heated at 80° C. overnight. The reaction mixture was filtered to obtain the precipitate. ¹H-NMR confirmed the product (294 mg, 58.8% yield).

Example 9

Synthesis of ethyl 2-((1-(tert-butoxycarbonyl)peperidin-4-yl)amino)-6-oxo-1,6-dihydropyrimidine-5-carboxylate

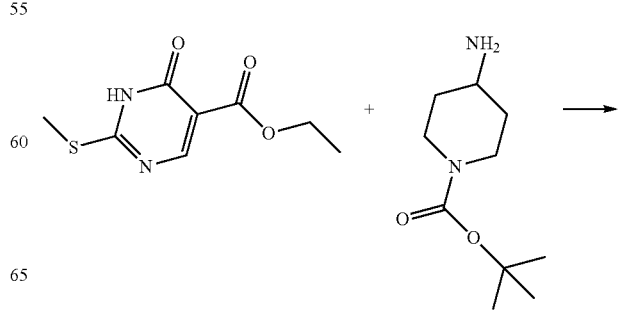

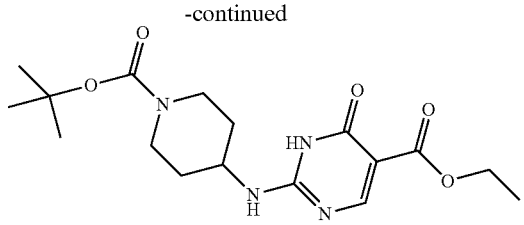

Ethyl 2-(methylthio)-6-oxo-1,6-dihyropyrimidine-5-carboxylate (292 mg, 1.365 mmol) and tert-butyl-4-aminopiperidine-1-carboxylate (273 mg, 1.365 mmol) were dissolved in 10 mL of ethanol and heated at 80° C. overnight. The precipitate was not evident so the solution was heated to 90° C. overnight. The final product was then recovered.

Example 10

Synthesis of ethyl 2-((1-benzylpeperidin-4-yl)amino)-6-oxo-1,6-dihydropyrimidine-5-carboxylate

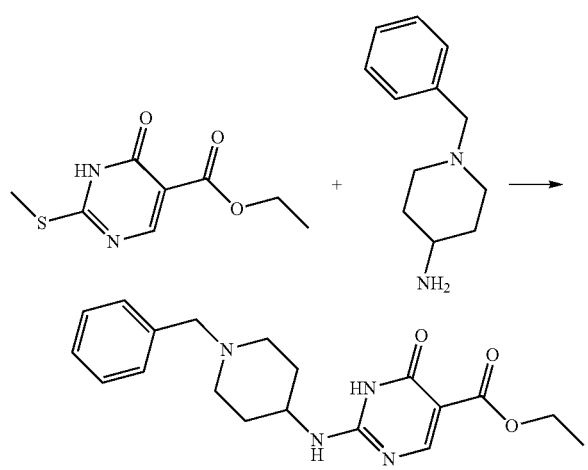

Ethyl 2-(methylthio)-6-oxo-1,6-dihyropyrimidine-5-carboxylate (301 mg, 1.403 mmol) and 1-benzylpiperidine-4-amine (267 mg, 1.403 mmol) were dissolved in 10 mL of ethanol and heated at 80° C. overnight. The precipitate was not evident so the solution was heated to 90° C. overnight. The final product was then recovered.

Example 11

Synthesis of ethyl 2-((1-benzylpyrrolidin-3-yl)amino)-6-oxo-1,6-dihydropyrimidine-5-carboxylate

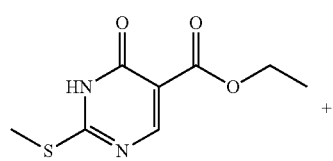

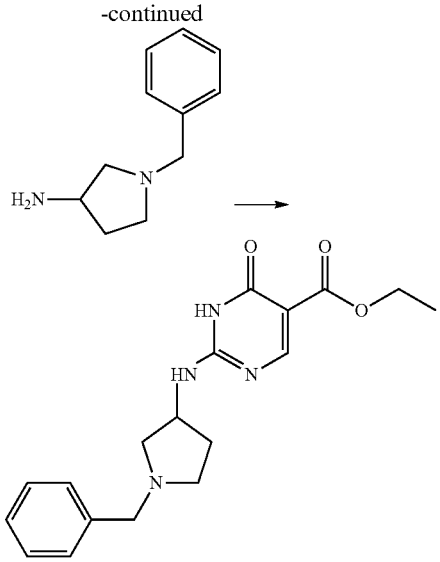

Ethyl 2-(methylthio)-6-oxo-1,6-dihyropyrimidine-5-carboxylate (313 mg, 1.460 mmol) and 1-benzylpyrrolidin-3-amine (257 mg, 1.460 mmol) were dissolved in 10 mL of ethanol and heated at 80° C. overnight. The precipitate was not evident so the solution was heated to 90° C. overnight. The final product was then recovered.

Example 12

Synthesis of Ethyl 2-((4-chlorophenethyl)amino)-6-oxo-1,6-dihydropyrimidine-5-carboxylate (HGN-0038)

The mixture of ethyl 2-(methylthio)-6-oxo-1,6-dihyropyrimidine-5-carboxylate (333 mg, 1.554 mmol) and 2-(4-chlorophenyl)ethanamine (242 mg, 1.554 mmol) were dissolved in 10 mL of ethanol and heated at 80° C. overnight. After heating, the solution was run on thin layer chromatography and filtered. The precipitate was collected and stored. ¹H-NMR confirmed the product (126 mg, 25.2% yield).

Example 13

Synthesis of Ethyl 2-([1,1'-biphenyl]-3-ylamino)-6-oxo-1,6-dihydropyrimidine-5-carboxylate

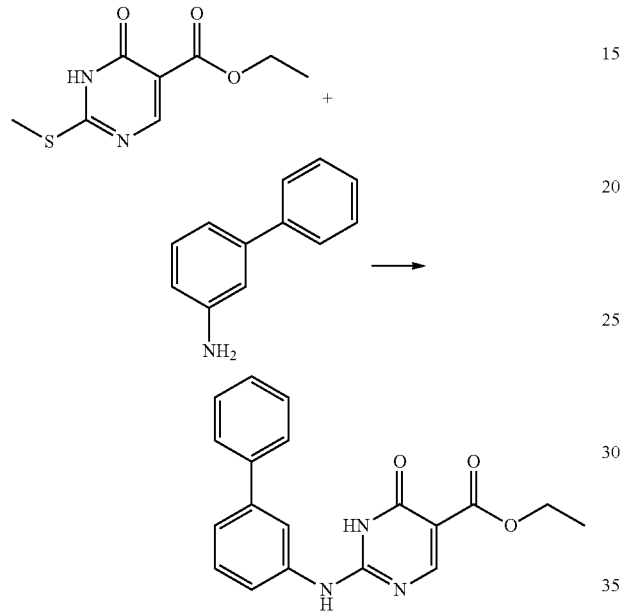

The mixture of ethyl 2-(methylthio)-6-oxo-1,6-dihyropyrimidine-5-carboxylate (319 mg, 1.491 mmol) and [1,1'-biphenyl]-3-amine (252 mg, 1.491 mmol) were dissolved in 10 mL of ethanol and heated at 80° C. overnight. After heating, the solution was run on thin layer chromatography and filtered. The precipitate was collected and stored. ¹H-NMR confirmed the product (246 mg, 49.2%).

Example 14

Synthesis of Ethyl 2-([1,1'-biphenyl]-2-ylamino)-6-oxo-1,6-dihydropyrimidine-5-carboxylate

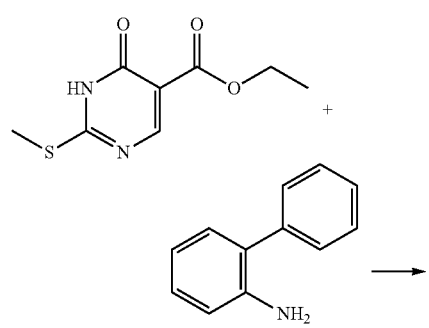

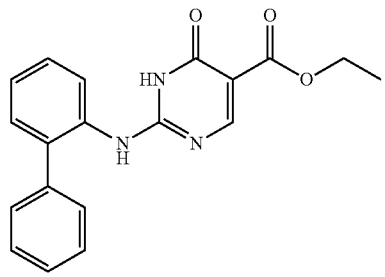

The mixture of ethyl 2-(methylthio)-6-oxo-1,6-dihyropyrimidine-5-carboxylate (319 mg, 1.491 mmol) and [1,1'-biphenyl]-2-amine (252 mg, 1.491 mmol) were dissolved in 10 mL of ethanol and heated at 80° C. overnight. After heating, the solution was run on thin layer chromatography and filtered. The precipitate was collected and stored. ¹H-NMR confirmed the product.

Example 15

Synthesis of Ethyl 6-oxo-2-((4-piperidin-1-yl)amino)-1,6-dihydropyrimidine-5-carboxylate (HGN-0034)

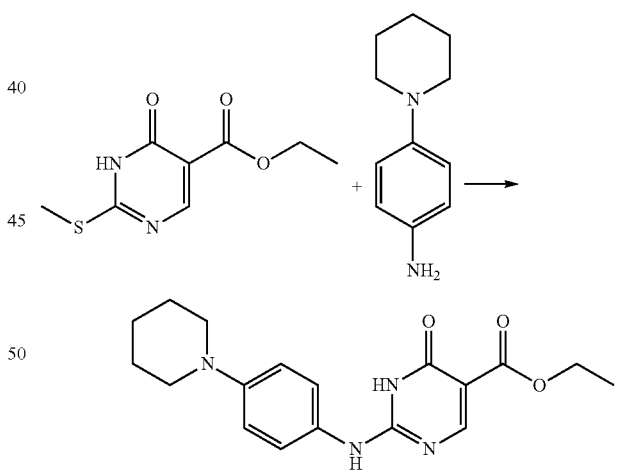

The mixture of ethyl 2-(methylthio)-6-oxo-1,6-dihyropyrimidine-5-carboxylate (313 mg, 1.460 mmol) and 4-(piperidin-1yl)aniline (257 mg, 1.460 mmol) were dissolved in 10 mL of ethanol and heated at 80° C. overnight. After heating, the solution was run on thin layer chromatography and filtered. The precipitate was collected and stored. ¹H-NMR confirmed the product (HGN-0034) (272 mg, 54.4% yield).

Example 16

Synthesis of Ethyl 2-(methylthio)-6-oxo-1,6-dihydropyrimidine-5-carboxylate

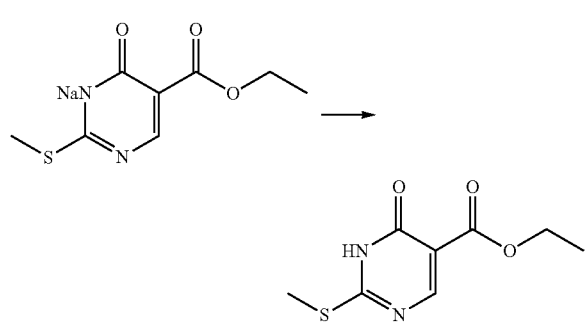

Ethyl sodium 5-(ethoxycarbonyl)-2-(methylthio)-4-oxo-4H-pyrimidin-3-ide (3.31 g, 14.00 mmol) was dissolved in 300 mL of methanol. 2 mL of HCl was added to the solution, which was condensed to yield the product.

Example 17

Synthesis of Ethyl 2-((1H-indazol-6-yl)amino)-6-oxo-1,6-dihydropyrimidine-5-carboxylate (HGN-0040)

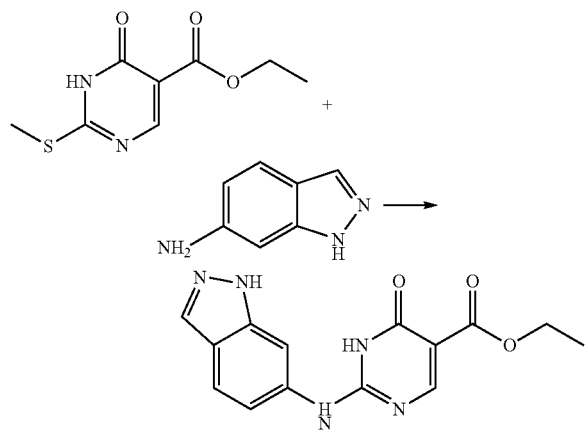

The mixture of ethyl 2-(methylthio)-6-oxo-1,6-dihyropyrimidine-5-carboxylate (358 mg, 1.671 mmol) and 1-H-indazol-6-amine (222 mg, 1.671 mmol) were dissolved in 10 mL of ethanol and heated at 80° C. overnight. After heating, the solution was run on thin layer chromatography and filtered. The precipitate was collected and stored. $^1$H-NMR confirmed the product (227 mg, 45.4% yield).

Example 18

Synthesis of Ethyl 2-((2,3-dihydro-1H-inden-2-yl)amino)-6-oxo-1,6-dihydropyrimidine-5-carboxylate

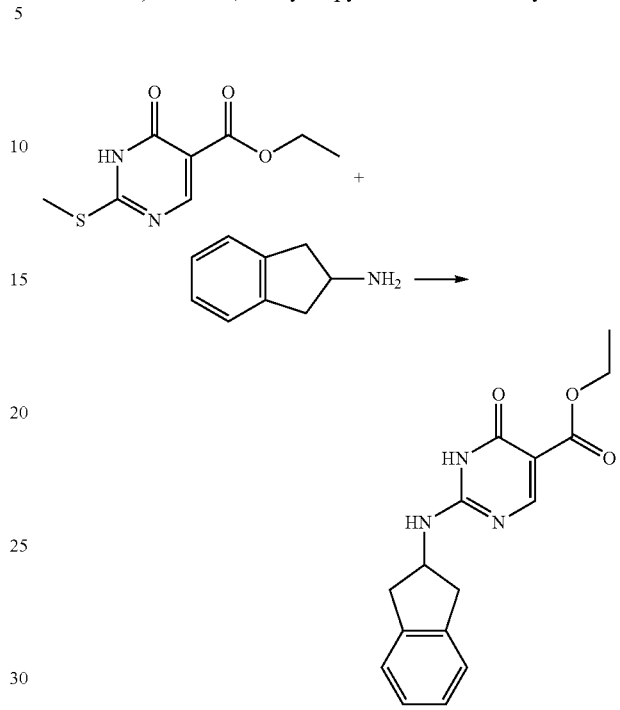

The mixture of ethyl 2-(methylthio)-6-oxo-1,6-dihyropyrimidine-5-carboxylate (358 mg, 1.67 mmol) and 2,3-dihyrdro-1H-inden-2-amine (222 mg, 1.67 mmol) were dissolved in 10 mL of ethanol and heated at 80° C. overnight. Precipitate was not evident so the solution was heated up to 90° C. overnight. The product was then recovered.

Example 19

Synthesis of 2-(4-((5-(ethoxycaronyl)-6-oxo-1,6-dihydropyrimidin-2-yl)amino)phenyl)acetic acid (HGN-0041)

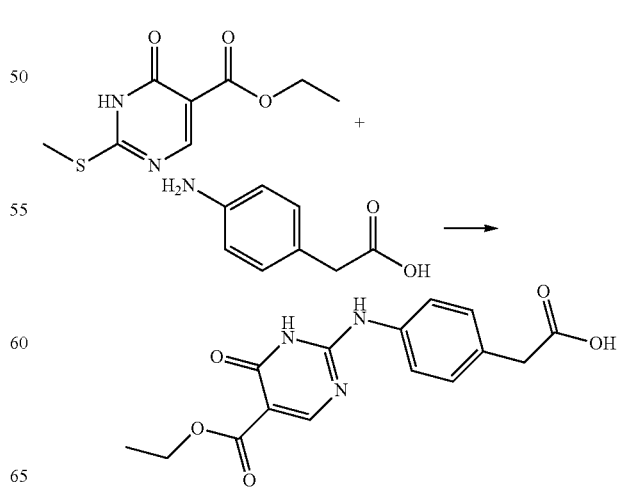

The mixture of ethyl 2-(methylthio)-6-oxo-1,6-dihyropyrimidine-5-carboxylate (338 mg, 1.576 mmol) and 2-(4-aminophenyl)acetic acid (238 mg, 1.576 mmol) were dissolved in 10 mL of ethanol and heated at 80° C. overnight. After heating, the solution was run on thin layer chromatography and filtered. The precipitate was collected and stored. $^1$H-NMR confirmed the product (HGN-0041) (235 mg, 47%).

Example 20

Synthesis of Ethyl 2-((1H-indazol-5-yl)amino)-6-oxo-1,6-dihydropyrimidine-5-carboxylate (HGN-0042)

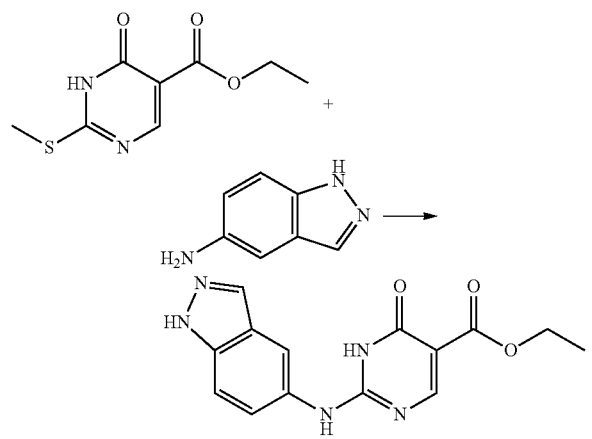

The mixture of ethyl 2-(methylthio)-6-oxo-1,6-dihyropyrimidine-5-carboxylate (358 mg, 1.671 mmol) and 1H-indazol-5-amine (222 mg, 1.671 mmol) were dissolved in 10 mL of ethanol and heated at 80° C. overnight. After heating, the solution was run on thin layer chromatography and filtered. The precipitate was collected and stored. $^1$H-NMR confirmed the product (HGN-0042) (441 mg, 88% yield).

Example 21

Synthesis of Sodium 2-((4-morpholinophenyl)amino)-4-oxidopyrimidine-5-carboxylate

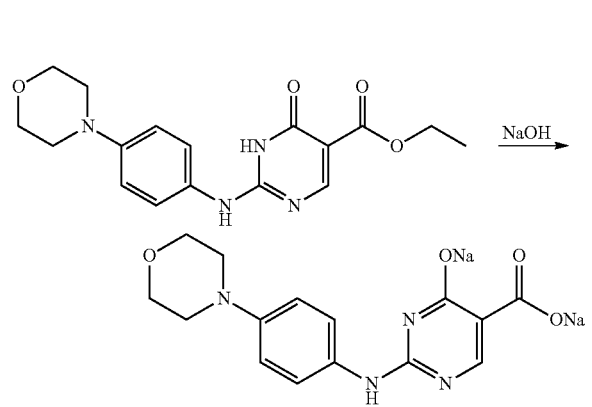

The mixture of ethyl 2-((4-morpholinophenyl)amino)-6-oxo-1,6-dihydropyrimidine-5-carboxylate (210 mg, 0.610 mmol) and sodium hydroxide (1M) were heated at 105° C. for 4 hours followed by heating at 40° C. overnight. Then the solution was condensed to recover the final product (290 mg, 132% yield). $^1$H-NMR confirmed the product.

Example 22

Synthesis of Sodium 2-([1,1'-biphenyl]-3-ylamino)-4-oxidopyrimidine-5-carboxylate (HGN-0044)

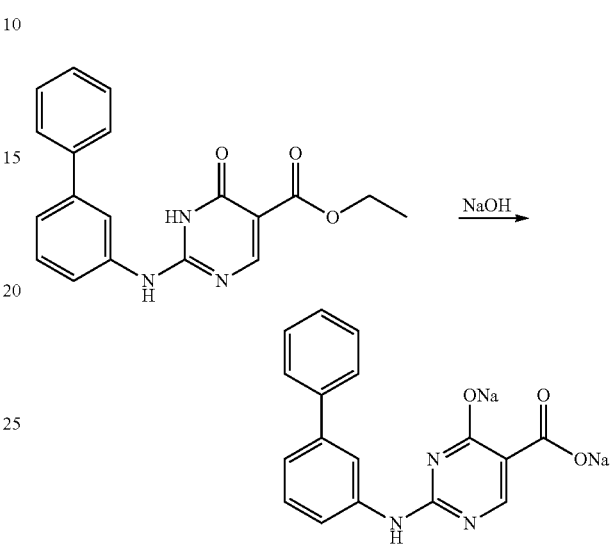

The mixture of ethyl 2-(([1,1'-biphenyl]-3-ylamino)-6-oxo-1,6-dihydropyrimidine-5-carboxylate (179 mg, 0.534 mmol) and sodium hydroxide (1M) were heated at 105° C. for 4 hours followed by heating at 40° C. overnight. Then the solution was condensed to recover the final product. $^1$H-NMR confirmed the product (HGN-0044) (170 mg, 91% yield).

Example 23

Synthesis of Sodium 4-oxido-2-((piperidin-1-yl)phenyl)amino)pyrimidine-5-carboxylate (HGN-0036)

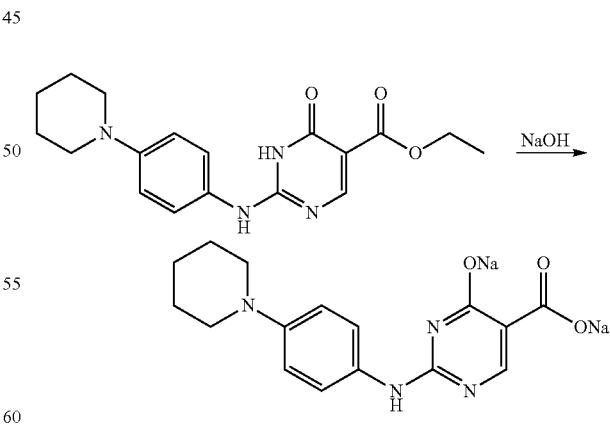

The mixture of ethyl 6-oxo-2-((4-(piperidin-1-yl)phenyl)amino-1,6-dihydropyrimidine-5-carboxylate (219 mg, 0.64 mmol) and sodium hydroxide (1M) were heated at 105° C. for 4 hours followed by heating at 40° C. overnight. Then the solution was condensed to recover the final product. $^1$H-NMR confirmed the product (240 mg, 105% yield).

Example 24

Synthesis of Sodium 2-((1H-indazol-6-yl)amino)-4-oxoidopyrimidine-5-carboxylate (HGN-0045)

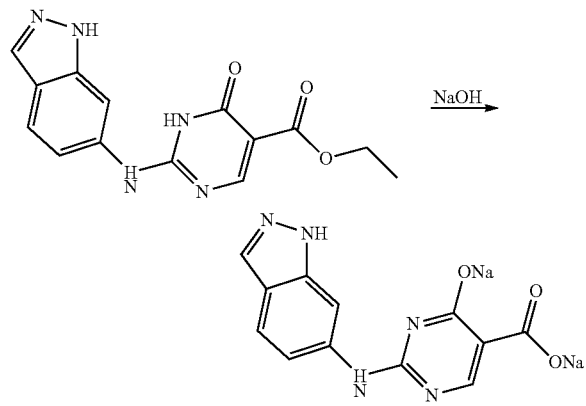

The mixture of ethyl 2-((1H-indazol-6-yl)amino)-6-oxo-1,6-dihydropyrimidine-5-carboxylate (144 mg, 0.481 mmol) and sodium hydroxide (1M) were heated at 105° C. for 4 hours followed by heating at 40° C. overnight. Then the solution was condensed to recover the final product. $^1$H-NMR confirmed the product (140 mg, 92% yield).

Example 25

Synthesis of Sodium 2-((4-(carboxylatetomethyl)phenyl)amino)-4-oxoidopyrimidine-5-carboxylate

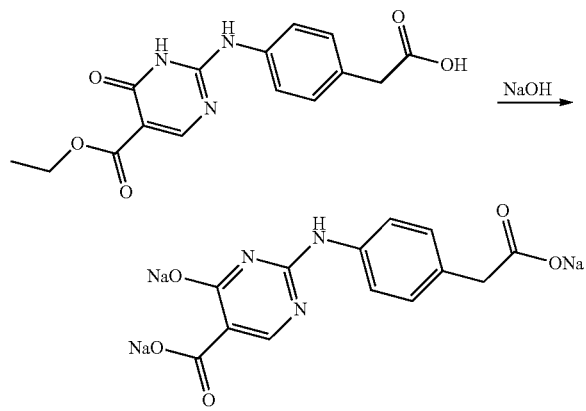

The mixture of 2-(4-((5-(ethoxycarbonyl)-6-oxo-1,6-dihyrdropyrimidin-2-yl)amino)phenyl)acetic acid (206 mg, 0.649 mmol) and sodium hydroxide (1M) were heated at 105° C. for 4 hours followed by heating at 40° C. overnight. Then the solution was condensed to recover the final product. $^1$H-NMR confirmed the product.

Example 26

Synthesis of Sodium 2-((1H-indazol-5-yl)amino)-4-oxoidopyrimidine-5-carboxylate (HGN-0046)

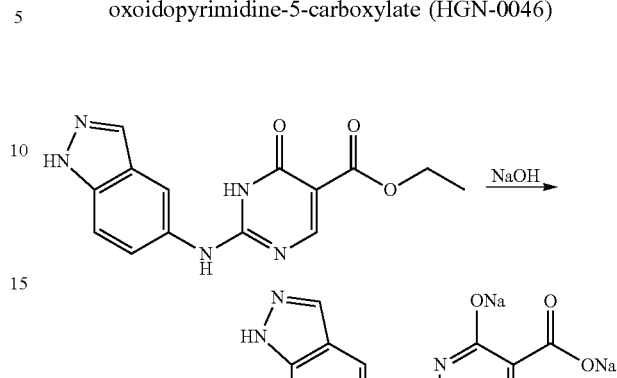

The mixture of ethyl 2-((1H-indazol-5-yl)amino)-6-oxo-1,6-dihydropyrimidine-5-carboxylate (292 mg, 0.976 mmol) and sodium hydroxide (1M) were heated at 105° C. for 4 hours followed by heating at 40° C. overnight. Then the solution was condensed to recover the final product. $^1$H-NMR confirmed the product (300 mg, 98% yield).

Example 27

Synthesis of Ethyl 2-((furan-2-ylmethyl)amino)-6-oxo-1,6-diydropyrimidine-5-carboxylate (HGN-0047)

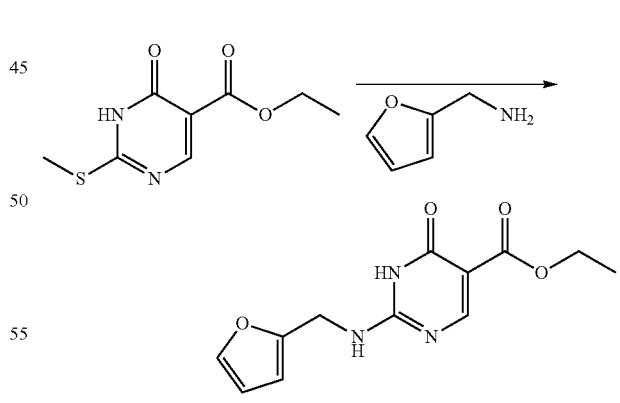

The mixture of ethyl 2-(methylthio)-6-oxo-1,6-dihydropyrimidine-5-carboxylate (300 mg, 1.4 mmol) and furan-2-ylmethanamine (136 mg, 1.4 mmol) were mixed in ethanol and refluxed overnight. The precipitate was filtered to recover the final product. $^1$H-NMR confirmed the product (200 mg, 54.3% yield).

Example 28

Synthesis of Ethyl 2-((furan-2-ylmethyl)amino)-6-oxo-1,6-diydropyrimidine-5-carboxylic acid

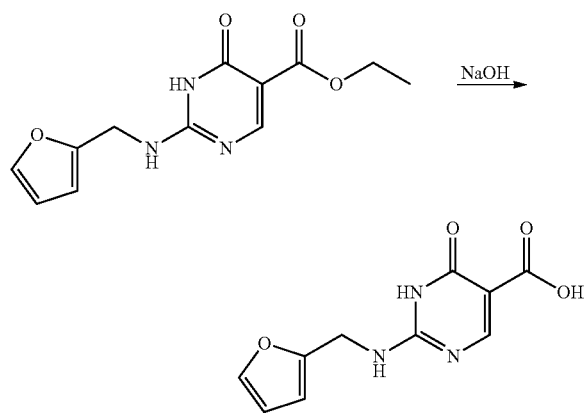

Ethyl 2-((furan-2-ylmethyl)amino)-6-oxo-1,6-diydropyrimidine-5-carboxylate (HGN-0047) (150 mg, 0.57 mmol) was suspended in 5 mL of dioxane and then 1M NaOH was added dropwise. The reaction mixture was heated under reflux for 4 hours and at room temperature overnight. The solvent was removed and $^1$H-NMR confirmed the product (204 mg, 152% yield).

Example 29

Synthesis of 6-oxo-2-((((tetrahydrofuran-2-yl)methyl)amino)-1,6-diydropyrimidine-5-carboxylic acid

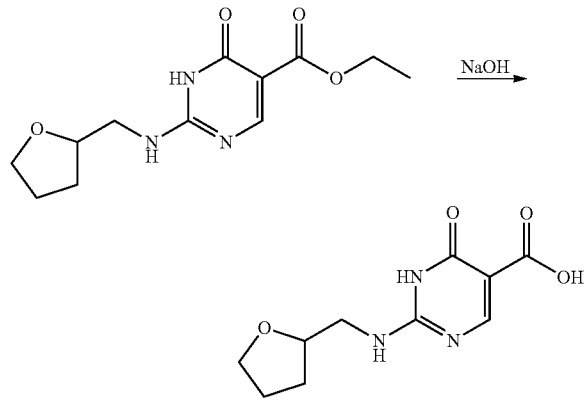

Ethyl 6-oxo-2-((((tetrahydrofuran-2-yl)methyl)amino)-1,6-diydropyrimidine-5-carboxylate (126 mg, 0.471 mmol) was suspended in 5 mL of dioxane and then 1M NaOH was added dropwise. The reaction mixture was heated under reflux for 4 hours and at room temperature overnight. The solvent was removed and $^1$H-NMR confirmed the product (191 mg, 169% yield).

Example 30

Synthesis of ethyl 6-oxo-2-(phenylamino)-1,6-diydropyrimidine-5-carboxylate

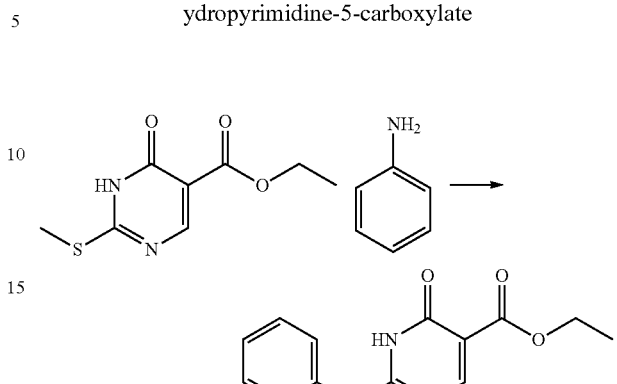

Ethyl 2-(methylthio)-6-oxo-1,6-dihydropyrimidine-5-carboxylate (1 g, 4.67 mmol) was added into a stirred solution of aniline (522 mg, 5.60 mmol). The reaction mixture was heated to 160° C. for 2 hours. The reaction mixture was cooled down and recrystalized in DMF with water (1:1). The mixture was filtered and titrated the residue with ethanol. $^1$H-NMR confirmed the product (about 100 mg).

$^1$H-NMR: δ1.22 (t, 3H, CH$_3$), δ4.2 (q, 2H, CH$_2$), δ7.1 (t, 1H, H-Ph C4), δ7.3 (t, 2H, H-Ph C3), δ7.6 (d, 2H, H-Ph C2), δ8.0 (s, 1H, NH), δ8.5 (s, 1H, H-pyrimidine)

Example 31

Synthesis of ethyl 6-oxo-2-(thiazol-2-ylamino)-1,6-diydropyrimidine-5-carboxylate

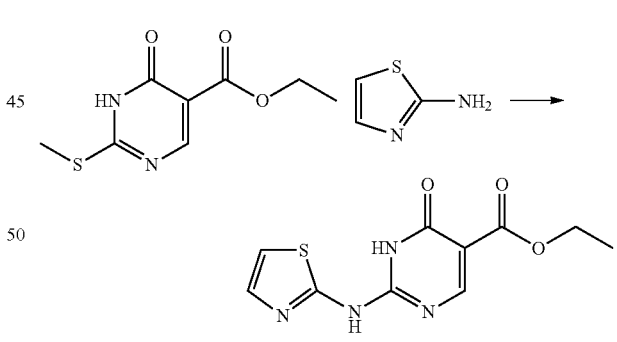

Ethyl 2-(methylthio)-6-oxo-1,6-dihydropyrimidine-5-carboxylate (1 g, 4.67 mmol) was added into a stirred solution of thiazol-2-amine (561 mg, 5.60 mmol). The reaction mixture was heated to 160° C. for 2 hours. Then the reaction mixture was cooled down and recrystalized in DMF with water (1:1). The mixture was filtered and titrated the residue with ethanol. $^1$H-NMR confirmed the product (about 300 mg).

$^1$H-NMR: δ1.35 (t, 3H, H—CH$_3$), δ4.15 (q, 2H, H—CH$_2$), δ7.1 (t, 1H, H-thiazol C5), δ7.4 (d, 1H, H-thiazol C4), δ8.48 (s, 1H, H-pyrimidine)

Example 32

Synthesis of 6-oxo-2-(phenylamino)-1,6-diydropyrimidine-5-carboxylic acid

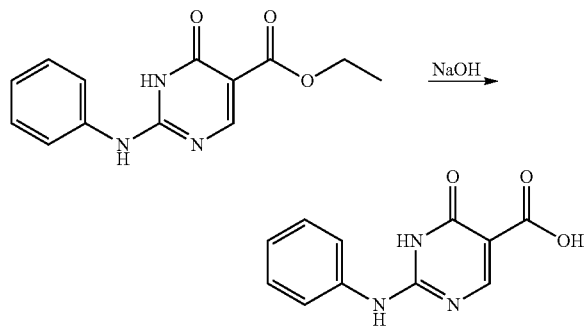

Sodium hydroxide (1M) was added to ethyl 6-oxo-2-(phenylamino)-1,6-dihydropyrimidine-5-carboxylate (0.1 g, 0.386 mmol) in 1 mL methanol and stirred at 80° C. for 2 hours and then 40° C. overnight. Then the reaction mixture was cooled down, and the solvent was removed. The reaction mixture was then diluted with water and the pH was adjusted to about 3.0. The reaction mixture was filtered, and the solid was collected and dried. ¹H-NMR confirmed the structure (about 10 mg).

¹H-NMR: δ7.1 (t, 1H, H-Ph C4), δ7.3 (t, 2H, H-Ph C3), δ7.6 (d, 2H, H-Ph C2), δ8.0 (s, 1H, NH), δ8.5 (s, 1H, H-pyrimidine), δ9.7 (s, 1H, OH).

Example 33

Synthesis of 6-oxo-2-(thiazol-2-ylamino)-1,6-diydropyrimidine-5-carboxylic acid

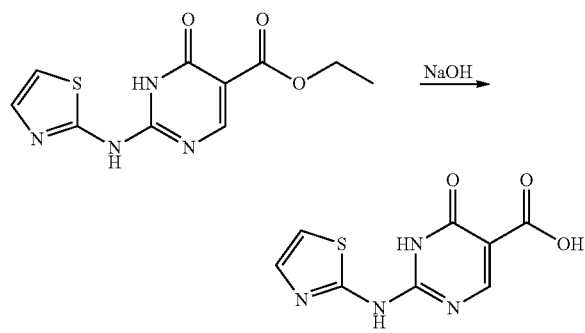

Sodium hydroxide (1M) was added to ethyl 6-oxo-2-(thiazol-2-ylamino)-1,6-dihydropyrimidine-5-carboxylate (360 mg, 1.352 mmol) in 1 mL methanol and stirred at 80° C. for 2 hours and then 40° C. overnight. Then the reaction mixture was cooled down, and the solvent was removed. The reaction mixture was then diluted with water and the pH was adjusted to about 3.0. The reaction mixture was filtered, and the solid was collected and dried. ¹H-NMR confirmed the structure (about 20 mg).

¹H-NMR: δ7.1 (d, 1H, H-thiazol C5), δ7.4 (d, 1H, H-thiazol C4), δ8.48 (s, 1H, H-pyrimidine), δ9.5 (s, 1H, OH).

Example 34

Synthesis of 2-4-bromophenyl)amino)-6-oxo-1,6-diydropyrimidine-5-carboxylic acid

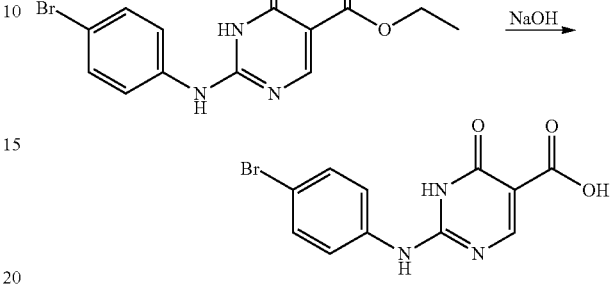

Sodium hydroxide (1M) was added to ethyl 2-((4-bromophenyl)amino)-6-oxo-1,6-dihydropyrimidine-5-carboxylate (155 mg, 0.458 mmol) in 2 mL dioxane and hydrolyzed at 80° C. for 2 hours and then 40° C. overnight. Then the reaction mixture was cooled down, and the dioxane was removed. The reaction mixture was then acidified with IN HCl so the pH was adjusted to about 3.0. The reaction mixture was filtered, and the solid was collected and dried. ¹H-NMR confirmed the structure.

Example 35

IspF Binding Inhibition

Binding affinities between IspF and compounds synthesized herein were measured by surface plasmon resonance (SPR).

Methods

The binding constants of synthesized inhibitors were analyzed using surface plasmon resonance (SPR). All SPR experiments were performed using a Reichert SR7500DC instrument (Reichert, N.Y, USA) with carboxymethyl dextran hydrogel surface sensor chips (500,000 Dalton molecular weight carboxymethyl dextran chips, Reichert, N.Y, USA). IspF was immobilized using amine-coupling chemistry. The sensor chip surface was activated with a 10 min injection of a mixture of 11.5 mg/mL N-hydroxysucciniminde and 76.5 mg/mL 1-ethyl-3-(3-dimethylamino propyl) carbodiimide hydrochloride at a flow rate of 20 µl/min. IspF was diluted to final concentration of 60 µg/ml with 5 mM acetate buffer, pH 5.0 and immobilized with a 10 min injection over the left channel at a flow rate of 20 µl/min. Typically, 3000 µRIU-4000 µRIU of IspF was immobilized. To quench excess succinaminde ester groups, 1M Ethanolamine, pH 8.5 was injected for 4 min at a 50 µl/min flow rate. All SPR experiments were performed at 25° C. using PBS-D (50 mM sodium phospate/pH 7.4, 150 mM sodium chloride, and 5% DMSO) as a running buffer at a 50 µl/min flow rate. Inhibitors were initially dissolved in DMSO. Samples were diluted such that 5% DMSO was maintained in all samples. A concentration series of inhibitor, as well as periodic buffer injections, were individually injected and collected for approximately 5 minutes. Data were analyzed using Scrubber2 (Biologic Software).

Results

The binding affinity between IspF inhibitor compounds and IspF were measured by SPR. The results can be used as a screening tool to indicate which compounds should be evaluated further. The results are provided in terms of the dissociation constant ($K_d$) between IspF and the inhibitor compounds. No binding indicated a lack of inhibition. Lower concentrations indicated a higher degree of inhibition.

TABLE 1

BINDING AFFINITY IspF INHIBITORS AND IspF

| Inhibitor | $K_d$ |
|---|---|
| HGN-0001 | no binding |
| HGN-0002 | not soluble |
| HGN-0003 | 82 uM |
| HGN-0005 | 176 uM |
| HGN-0013 | non-specific |
| HGN-0018 | no binding |
| HGN-0019 | 380 uM |
| HGN-0020 | 204 uM |
| HGN-0024 | 784 uM |
| HGN-0025 | no binding |
| HGN-0026 | no binding |
| HGN-0027 | no binding |
| HGN-0028 | 305 uM |
| HGN-0030 | 178 uM |
| HGN-0035 | not soluble |
| HGN-00037 | not soluble |
| HGN-0038 | not soluble |
| HGN-0039 | non specific |
| HGN-0040 | no binding |
| HGN-0041 | not soluble |
| HGN-0042 | not soluble |
| HGN-0045 | non specific |
| HGN-0046 | non specific |
| HGN-0048 | 486 uM |
| HGN-0052 | no binding |
| HGN-0055 | no binding |
| HGN-0056 | no binding |
| HGN-0060 | not soluble |
| HGN-0061 | no binding |
| HGN-0062 | no binding |
| HGN-0063 | 10.7 mM |

Example 36

Growth Inhibition of *Burkholderia* Spp. by IspF Inhibitor Compounds

Growth inhibition properties of compounds HGN-0023, HGN-0027, HGN-0028, and HGN-0029 against *B. thailandensis* E264 and *B. pseudomallei* 1026b and Bp340 were evaluated.

Methods

Overnight cultures of *Burkholderia* strains (obtained from Herbert Schweizer at the University of Colorado) were grown in low-salt LB (LSLB; 10 g/L tryptone, 5 g/L yeast extract, 1.25 g/L NaCl) at 37° C. The *Burkholderia* strains were diluted to 0.2 $OD_{600}$ in LSLB. Stocks of HGN compounds (40 mM in DMSO, except HGN-0028 at 20 mM) were diluted to 1 mM, then two-fold dilutions (1 mL each) in LSLB (500 μM, 250 μM, 125 μM, 62.5 μM, 31.25 μM) were prepared. In a 96-well microtiter plate, 160 μL of the inhibitor in LSLB at each concentration were added to the wells in triplicate. Then 40 μL of the 0.2 $OD_{600}$ bacterial suspension to was added each well (final $OD_{600}$=0.04, total well volume=200 μL). As controls, 40 μL of LSLB, DMSO, or kanamycin were added (final concentration 300 μg/mL) to wells in triplicate. The plates were incubated for 20 h at 37° C. with shaking in an Infinite M200 plate reader (Tecan Group Ltd., Männedorf, Switzerland). The plate was read at 15 min. intervals at 600 nm wavelength. The $OD_{600}$ values were graphed over time (FIGS. 1-6).

Results

Initial results (FIG. 1) indicated several candidate compounds to further evaluate inhibition of the growth of *B. pseudomallei*. From FIG. 2, tests indicated that HGN-0027 and HGN-0028 inhibited the growth of *B. pseudomallei* over time. Further study tested the concentration effects of HGN-0023, -0027, -0028, and -0029 on the the growth of *B. pseudomallei* over time. These studies confirmed that HGN-0023 (FIG. 3) and HGN-0029 (FIG. 6) did not inhibit the growth of *B. pseudomallei*. Whereas, HGN-0027 was a potent inhibitor, at multiple concentrations, of the growth of *B. pseudomallei* (FIGS. 4, 7, and 8). HGN-0028 was dose dependent in its ability to inhibit *B. pseudomallei* growth (FIGS. 5, 9. and 10). Lower concentrations of HGN-0028 did not inhibit *B. pseudomallei* growth.

Example 37

The compounds can be grouped by chemical class, Pyrimidine IspF inhibitors (Table 2), Imidazole IspF inhibitors (Table 3), Fusion IspF inhibitors (Table 4), and miscellaneous IspF inhibitors (Table 5). The tables below also summarize the bacterial inhibition of the compounds.

TABLE 2

Pyrimidine IspF inhibitors

| | | | % Growth Inhibition[a] | |
|---|---|---|---|---|
| Designation | Chemical Formula | Structure | Endpoint (24 h) | Growth Curve |
| HGN-0017 | $C_{12}H_{17}N_3O_4$ | 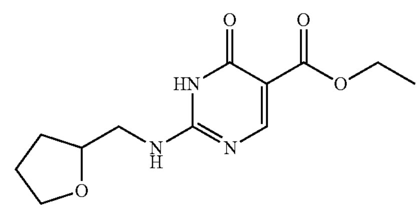 [SMILES: CCOC(=O)c1cnc(NCC2CCCO2)[nH]c1=O]  | ND | 0.00[b] |

TABLE 2-continued

Pyrimidine IspF inhibitors

| Designation | Chemical Formula | Structure | % Growth Inhibition[a] | |
|---|---|---|---|---|
| | | | Endpoint (24 h) | Growth Curve |
| HGN-0047 | $C_{12}H_{13}N_3O_4$ | | 0.00[b] | ND |
| HGN-0041 | $C_{15}H_{15}N_3O_5$ | | 0.00[b] | ND |
| HGN-0121 | $C_{14}H_{14}ClN_3O_3$ | | 0.00[b] | ND |
| HGN-0123 | $C_{14}H_{14}ClN_3O_3$ | | 0.00[b] | ND |
| HGN-0125 | $C_{14}H_{14}ClN_3O_3$ | | 23.89 ± 36.14 | ND |
| HGN-0038 | $C_{15}H_{16}ClN_3O_3$ | | 0.00[b] | ND |
| HGN-0119 | $C_{15}H_{16}ClN_3O_3$ | | 0.00[b] | ND |

TABLE 2-continued

Pyrimidine IspF inhibitors

| Designation | Chemical Formula | Structure | % Growth Inhibition[a] | |
|---|---|---|---|---|
| | | | Endpoint (24 h) | Growth Curve |
| HGN-0127 | $C_{14}H_{13}Cl_2N_3O_3$ | | 3.47 ± 2.20 | ND |
| HGN-0129 | $C_{14}H_{13}Cl_2N_3O_3$ | | 64.42 ± 2.77 | ND |
| HGN-0131 | $C_{15}H_{15}Cl_2N_3O_3$ | | 0.00[b] | ND |
| HGN-0117 | $C_{15}H_{15}Cl_2N_3O_3$ | | 0.00[b] | ND |
| HGN-0135 | C15H15Cl2N3O3 | | 0.00[b] | ND |
| HGN-0133 | $C_{14}H_{14}FN_3O_3$ | | 0.00[b] | ND |
| HGN-0113 | $C_{14}H_{14}FN_3O_3$ | | 0.00[b] | ND |

TABLE 2-continued

Pyrimidine IspF inhibitors

| Designation | Chemical Formula | Structure | % Growth Inhibition[a] | |
|---|---|---|---|---|
| | | | Endpoint (24 h) | Growth Curve |
| HGN-0111 | $C_{15}H_{16}FN_3O_3$ | | 31.31 ± 39.32 | ND |
| HGN-0115 | $C_{15}H_{16}FN_3O_3$ | | 0.00[b] | ND |
| HGN-0016 | $C_{13}H_{11}ClN_4O_4$ | | ND | ND |
| HGN-0040 | $C_{14}H_{13}N_5O_3$ | | 16.39 ± 6.29 | ND |
| HGN-0042 | $C_{14}H_{13}N_5O_3$ | | 20.70 ± 0.71 | ND |
| HGN-0034 | $C_{18}H_{22}N_4O_3$ | | 86.20 ± 0.16 | ND |
| HGN-0037 | $C_{19}H_{17}N_3O_3$ | | L[c] | ND |
| HGN-0033 | $C_{19}H_{17}N_3O_3$ | | 5.07 ± 2.01 | ND |

TABLE 2-continued

Pyrimidine IspF inhibitors

| Designation | Chemical Formula | Structure | % Growth Inhibition[a] | |
|---|---|---|---|---|
| | | | Endpoint (24 h) | Growth Curve |
| HGN-0039 | $C_{19}H_{17}N_3O_3$ | | 0.00[b] | ND |
| HGN-0015 | $C_{18}H_{16}N_4O_3$ | | ND | 14.43 ± 2.38 |
| HGN-0012 | $C_8H_6N_4O_3S$ | | ND | ND |
| HGN-0077 | $C_{16}H_{12}N_4O_3$ | | ND | ND |
| HGN-0079 | $C_{11}H_8BrN_3O_3$ | | ND | ND |
| HGN-0011 | $C_{11}H_9N_3O_3$ | | ND | ND |
| HGN-0035 | $C_{17}H_{13}N_3O_3$ | | 91.14 ± 1.18 | ND |

TABLE 2-continued

Pyrimidine IspF inhibitors

| Designation | Chemical Formula | Structure | % Growth Inhibition[a] | |
|---|---|---|---|---|
| | | | Endpoint (24 h) | Growth Curve |
| HGN-0050 | $C_{10}H_{11}N_3Na_2O_4$ | | 32.99 ± 9.22 | ND |
| HGN-0049 | $C_{10}H_7N_3Na_2O_4$ | | 12.25 ± 0.40 | ND |
| HGN-0126 | $C_{12}H_8ClN_3Na_2O_3$ | | 34.34 ± 3.24 | ND |
| HGN-0124 | $C_{12}H_8ClN_3Na_2O_3$ | | 30.67 ± 2.67 | ND |
| HGN-0122 | $C_{12}H_8ClN_3Na_2O_3$ | | 23.02 ± 8.79 | ND |
| HGN-0028 | $C_{13}H_{10}ClN_3Na_2O_3$ | | ND | 68.20 ± 2.12 |

TABLE 2-continued

Pyrimidine IspF inhibitors

| Designation | Chemical Formula | Structure | % Growth Inhibition[a] | |
|---|---|---|---|---|
| | | | Endpoint (24 h) | Growth Curve |
| HGN-0120 | $C_{13}H_{10}ClN_3Na_2O_3$ | | 80.30 ± 0.40 | ND |
| HGN-0118 | $C_{13}H_9Cl_2N_3Na_2O_3$ | | 94.50 ± 4.42 | ND |
| HGN-0128 | $C_{12}H_7Cl_2N_3Na_2O_3$ | | 37.46 ± 0.21 | ND |
| HGN-0130 | $C_{12}H_7Cl_2N_3Na_2O_3$ | | 45.59 ± 2.35 | ND |
| HGN-0132 | $C_{13}H_9Cl_2N_3Na_2O_3$ | | 72.24 ± 11.83 | ND |
| HGN-0136 | $C_{13}H_9Cl_2N_3Na_2O_3$ | | 16.71 ± 5.04 | ND |

TABLE 2-continued

Pyrimidine IspF inhibitors

| Designation | Chemical Formula | Structure | % Growth Inhibition[a] | |
|---|---|---|---|---|
| | | | Endpoint (24 h) | Growth Curve |
| HGN-0134 | $C_{12}H_8FN_3Na_2O_3$ | | 26.05 ± 6.37 | ND |
| HGN-0114 | $C_{12}H_8FN_3Na_2O_3$ | | 5.94 ± 5.46 | ND |
| HGN-0112 | $C_{13}H_{10}FN_3Na_2O_3$ | | 19.82 ± 16.53 | ND |
| HGN-0116 | $C_{13}H_{10}FN_3Na_2O_3$ | | 20.46 ± 3.47 | ND |
| HGN-0014 | $C_{11}H_6BrN_3Na_2O_3$ | | 15.52 ± 0.41 | ND |
| HGN-0045 | $C_{12}H_7N_5Na_2O_3$ | | 0.00[b] | ND |
| HGN-0046 | $C_{12}H_7N_5Na_2O_3$ | | 15.12 ± 4.25 | ND |

TABLE 2-continued

Pyrimidine IspF inhibitors

| Designation | Chemical Formula | Structure | % Growth Inhibition[a] | |
|---|---|---|---|---|
| | | | Endpoint (24 h) | Growth Curve |
| HGN-0036 | $C_{16}H_{16}N_4Na_2O_3$ | | 22.38 ± 21.24 | ND |
| HGN-0013 | $C_{16}H_{10}N_4Na_2O_3$ | | ND | 6.26 ± 1.00 |
| HGN-0044 | $C_{17}H_{11}N_3Na_2O_3$ | | 1.48 ± 7.90 | ND |

[a] Growth inhibition calculated relative to DMSO control
[b] Growth with inhibitor was equal to or greater than DMSO control
[c] Limited solubility prevented accurate determination of growth
ND, not done

TABLE 3

Imidazole IspF inhibitors.

| Designation | Chemical Formula | Structure | % Growth Inhibition[a] | |
|---|---|---|---|---|
| | | | Endpoint (24 h) | Growth Curve |
| HGN-0029 and HGN-0056 | $C_9H_8N_2O$ | | ND | 23.58 ± 0.54 |
| HGN-0018 | $C_{12}H_{14}N_2O$ | | ND | ND |

TABLE 3-continued

Imidazole IspF inhibitors.

| Designation | Chemical Formula | Structure | % Growth Inhibition[a] | |
|---|---|---|---|---|
| | | | Endpoint (24 h) | Growth Curve |
| HGN-0019 | $C_{14}H_{12}N_2O_2$ | 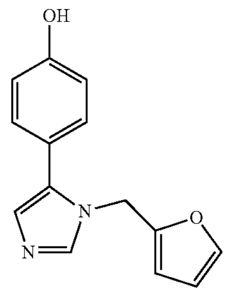 [SMILES: Oc1ccc(-c2cncn2Cc2ccco2)cc1] | ND | ND |
| HGN-0020 | $C_{19}H_{18}ClN_3O$ | 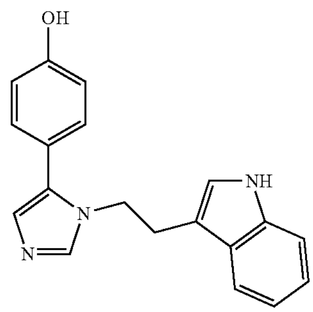 [SMILES: Oc1ccc(-c2cncn2CCc2c[nH]c3ccccc23)cc1] | ND | 1.26 ± 2.33 |
| HGN-0137 | $C_{20}H_{19}N_3O_2$ | 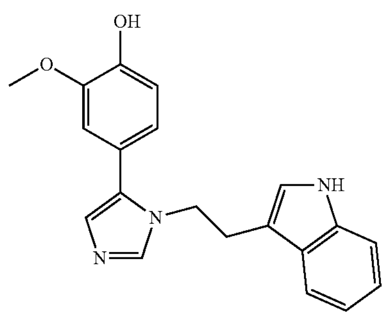 [SMILES: COc1cc(-c2cncn2CCc2c[nH]c3ccccc23)ccc1O] | 0.00[b] | ND |
| HGN-0021 | C16H14N2O | 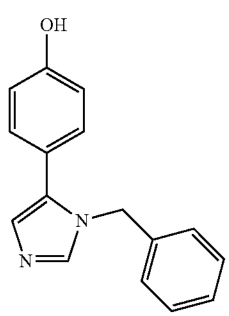 [SMILES: Oc1ccc(-c2cncn2Cc2ccccc2)cc1] | ND | ND |
| HGN-0022 and HGN-0052 (HCl salt) | $C_{17}H_{16}N_2O$ | 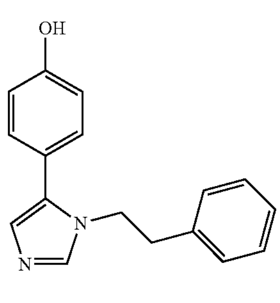 [SMILES: Oc1ccc(-c2cncn2CCc2ccccc2)cc1] | 0.00[b] | ND |

TABLE 3-continued
Imidazole IspF inhibitors.
| Designation | Chemical Formula | Structure | % Growth Inhibition[a] | |
|---|---|---|---|---|
| | | | Endpoint (24 h) | Growth Curve |
| HGN-0048 | $C_{17}H_{17}ClN_2O_2$ | 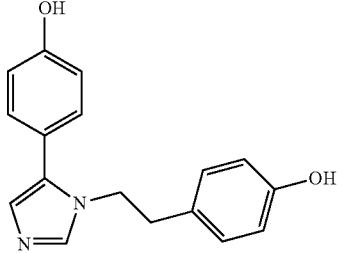 [SMILES: Oc1ccc(CCn2cncc2-c2ccc(O)cc2)cc1] | ND | ND |
| HGN-0091 | $C_{16}H_{13}ClN_2O$ | 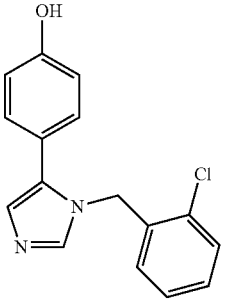 [SMILES: Oc1ccc(-c2cncn2Cc2ccccc2Cl)cc1] | L[c] | ND |
| HGN-0090 | $C_{16}H_{13}ClN_2O$ | 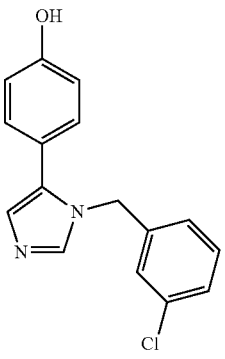 [SMILES: Oc1ccc(-c2cncn2Cc2cccc(Cl)c2)cc1] | L[c] | ND |
| HGN-0094 | $C_{16}H_{13}ClN_2O$ | 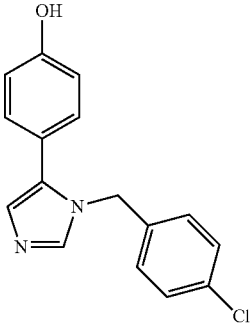 [SMILES: Oc1ccc(-c2cncn2Cc2ccc(Cl)cc2)cc1] | L[c] | ND |

TABLE 3-continued
Imidazole IspF inhibitors.
| Designation | Chemical Formula | Structure | % Growth Inhibition[a] | |
|---|---|---|---|---|
| | | | Endpoint (24 h) | Growth Curve |
| HGN-0108 | $C_{17}H_{15}ClN_2O$ | 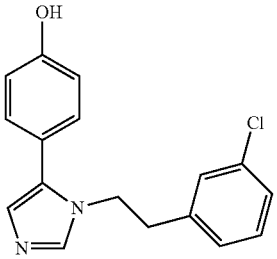 [SMILES: Oc1ccc(-c2cncn2CCc2cccc(Cl)c2)cc1] | L[c] | ND |
| HGN-0051 | $C_{17}H_{15}ClN_2O$ | 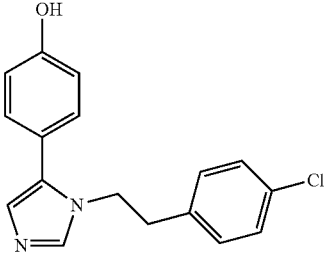 [SMILES: Oc1ccc(-c2cncn2CCc2ccc(Cl)cc2)cc1] | 0.00[b] | ND |
| HGN-0096 | $C_{17}H_{15}ClN_2O$ | 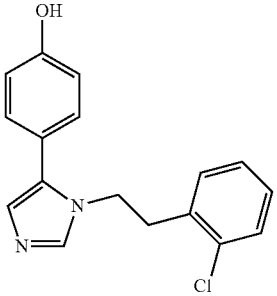 [SMILES: Oc1ccc(-c2cncn2CCc2ccccc2Cl)cc1] | L[c] | ND |
| HGN-0092 | $C_{16}H_{12}Cl_2N_2O$ | 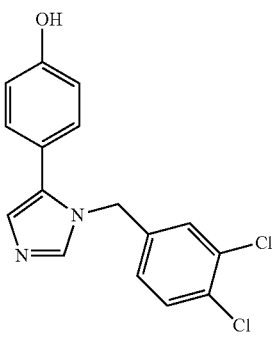 [SMILES: Oc1ccc(-c2cncn2Cc2ccc(Cl)c(Cl)c2)cc1] | 25.41 ± 2.79 | ND |
| HGN0098 | $C_{17}H_{14}Cl_2N_2O$ | 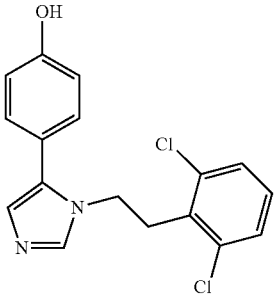 [SMILES: Oc1ccc(-c2cncn2CCc2c(Cl)cccc2Cl)cc1] | 0.00[b] | ND |

TABLE 3-continued
Imidazole IspF inhibitors.
| Designation | Chemical Formula | Structure | % Growth Inhibition[a] | |
|---|---|---|---|---|
| | | | Endpoint (24 h) | Growth Curve |
| HGN-0099 | $C_{17}H_{14}Cl_2N_2O$ | 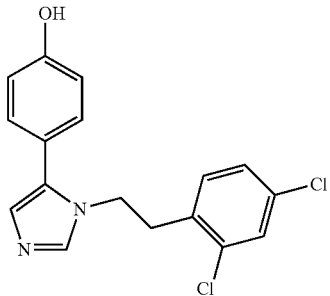 [SMILES: Oc1ccc(-c2cncn2CCc2ccc(Cl)cc2Cl)cc1] | 0.00[b] | ND |
| HGN-0100 | $C_{17}H_{14}Cl_2N_2O$ | 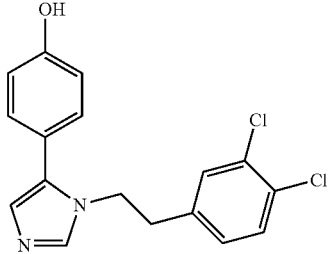 [SMILES: Oc1ccc(-c2cncn2CCc2ccc(Cl)c(Cl)c2)cc1] | L[c] | ND |
| HGN-0109 | $C_{16}H_{13}FN_2O$ | 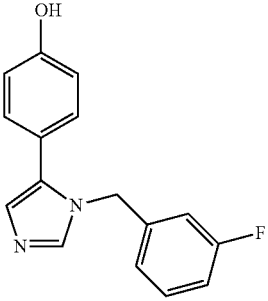 [SMILES: Oc1ccc(-c2cncn2Cc2cccc(F)c2)cc1] | 24.77 ± 10.79 | ND |
| HGN-0106 | $C_{16}H_{13}FN_2O$ | 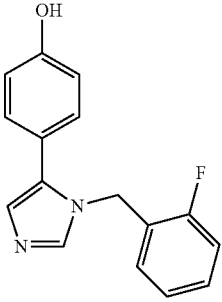 [SMILES: Oc1ccc(-c2cncn2Cc2ccccc2F)cc1] | 33.79 ± 16.09 | ND |

TABLE 3-continued

Imidazole IspF inhibitors.

| Designation | Chemical Formula | Structure | % Growth Inhibition[a] | |
|---|---|---|---|---|
| | | | Endpoint (24 h) | Growth Curve |
| HGN-0093 | $C_{16}H_{13}FN_2O$ | 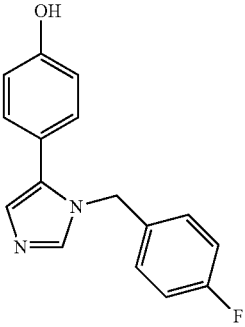 [SMILES: Oc1ccc(-c2cncn2Cc2ccc(F)cc2)cc1] | 58.12 ± 2.17 | ND |
| HGN-0095 | $C_{17}H_{15}FN_2O$ | 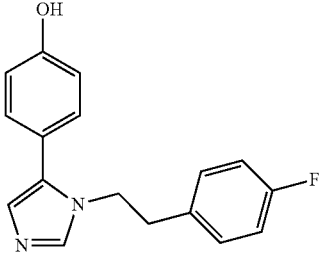 [SMILES: Oc1ccc(-c2cncn2CCc2ccc(F)cc2)cc1] | 88.27 ± 0.48 | ND |
| HGN-0097 | $C_{17}H_{15}FN_2O$ | 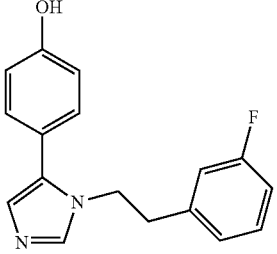 [SMILES: Oc1ccc(-c2cncn2CCc2cccc(F)c2)cc1] | 4.27 ± 14.54 | ND |
| HGN-0107 | $C_{17}H_{15}FN_2O$ | 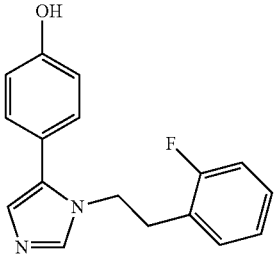 [SMILES: Oc1ccc(-c2cncn2CCc2ccccc2F)cc1] | 2.75 ± 2.62 | ND |

[a] Growth inhibition calculated relative to DMSO control
[b] Growth with inhibitor was equal to or greater than DMSO control
[c] Limited solubility prevented accurate determination of growth
ND, not done

TABLE 4

Fusion IspF inhibitors.

| Designation | Chemical Formula | Structure | % Growth Inhibition[a] | |
|---|---|---|---|---|
| | | | Endpoint (24 h) | Growth Curve |
| HGN-0005 | $C_{15}H_{17}N_5O_5$ | 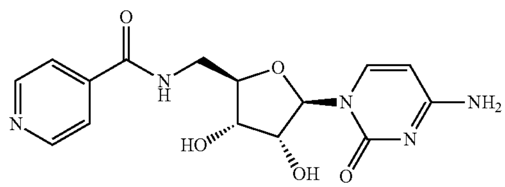 [SMILES: Nc1ccn([C@@H]2O[C@H](CNC(=O)c3ccncc3)[C@@H](O)[C@H]2O)c(=O)n1] | ND | 0.00[b] |
| HGN-0006 | $C_{15}H_{16}N_6O_5S$ | 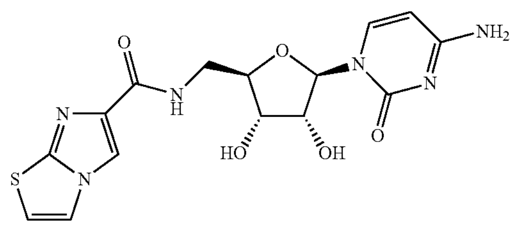 [SMILES: Nc1ccn([C@@H]2O[C@H](CNC(=O)c3cn4ccsc4n3)[C@@H](O)[C@H]2O)c(=O)n1] | 0.00[b] | ND |
| HGN-0007 | $C_{20}H_{19}F_6N_7O_9$ | 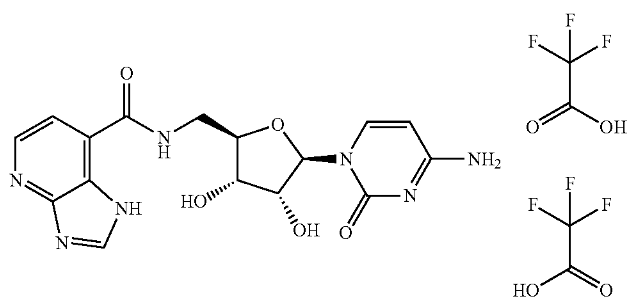 [SMILES: Nc1ccn([C@@H]2O[C@H](CNC(=O)c3ccnc4nc[nH]c34)[C@@H](O)[C@H]2O)c(=O)n1 ; O=C(O)C(F)(F)F ; O=C(O)C(F)(F)F] | 0.00[b] | ND |
| HGN-0008 | $C_{17}H_{19}F_6N_5O_{10}S$ | 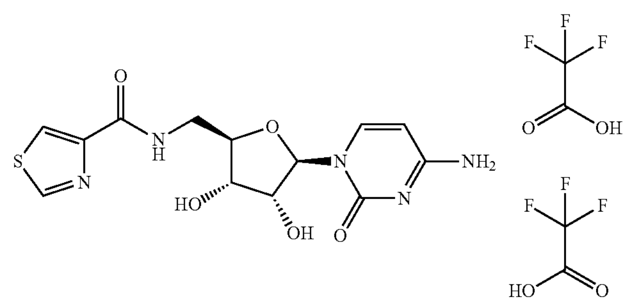 [SMILES: Nc1ccn([C@@H]2O[C@H](CNC(=O)c3cscn3)[C@@H](O)[C@H]2O)c(=O)n1 ; O=C(O)C(F)(F)F ; O=C(O)C(F)(F)F] | 0.00[b] | ND |
| HGN-0102 | $C_{16}H_{18}N_6O_5S$ | 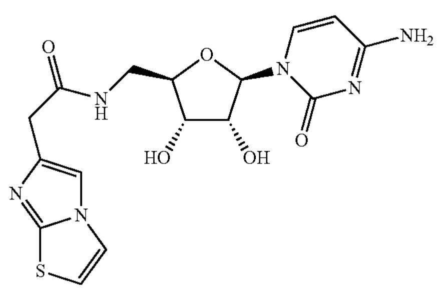 [SMILES: Nc1ccn([C@@H]2O[C@H](CNC(=O)Cc3cn4ccsc4n3)[C@@H](O)[C@H]2O)c(=O)n1] | 0.00[b] | ND |

[a]Growth inhibition calculated relative to DMSO control
[b]Growth with inhibitor was equal to or greater than DMSO control
ND, not done TABLE 5
Miscellaneous IspF inhibitors.
| Designation | Chemical Formula | Structure | % Growth Inhibition[a] | |
|---|---|---|---|---|
| | | | Endpoint (24 h) | Growth Curve |
| HGN-0031 | $C_{11}H_{12}N_2O$ | 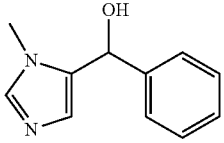 | ND | 0.00[b] |
| HGN-0061 | $C_{12}H_{14}N_2O$ | 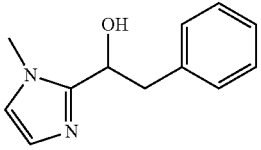 | ND | ND |
| HGN-0063 | $C_{17}H_{16}N_2O$ | 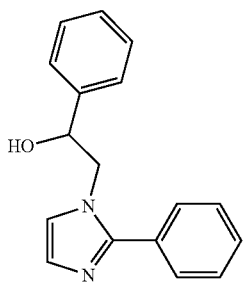 [SMILES: OC(Cn1ccnc1-c1ccccc1)c1ccccc1] | ND | ND |
| HGN-0060 | $C_{23}H_{20}N_2O$ | 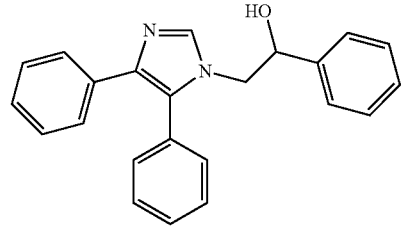 [SMILES: OC(Cn1cnc(-c2ccccc2)c1-c1ccccc1)c1ccccc1] | ND | ND |
| HGN-0062 | $C_{18}H_{18}N_2O$ | 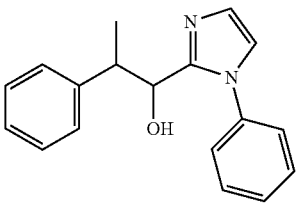 [SMILES: CC(c1ccccc1)C(O)c1nccn1-c1ccccc1] | ND | ND |
| HGN-0078 | $C_{10}H_9N_5$ | 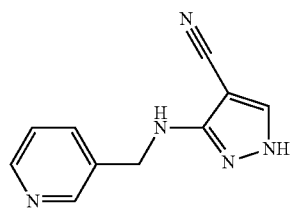 [SMILES: N#Cc1c[nH]nc1NCc1cccnc1] | ND | ND |
| HGN-0080 | $C_{10}H_{11}N_5O$ | 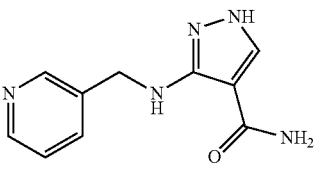 [SMILES: NC(=O)c1c[nH]nc1NCc1cccnc1] | ND | ND |

TABLE 5-continued

Miscellaneous IspF inhibitors.

| Designation | Chemical Formula | Structure | % Growth Inhibition[a] | |
|---|---|---|---|---|
| | | | Endpoint (24 h) | Growth Curve |
| HGN-0004 | $C_8H_7N_5O_2S$ | | 0.00[b] | ND |
| HGN-0002 | $C_{12}H_{10}N_6O_2$ | | ND | ND |
| HGN-0010 | $C_{10}H_8N_6O_2S$ | | 7.22 ± 4.24 | ND |
| HGN-0009 | $C_{11}H_{10}N_6O_2S$ | | 0.00[b] | ND |

[a]Growth inhibition calculated relative to DMSO control
[b]Growth with inhibitor was equal to or greater than DMSO control
ND, not done Example 38

Growth Inhibition of Malaria by IspF Inhibitor Compounds

The compounds described herein were also tested for their ability to inhibit the growth of the causative agent of malaria, Plasmodium falciparum, a protozoan parasite.

Methods

SYBR assay: The method of testing inhibition has been previously described (Co et al., 2009). Briefly, D6, C235 and W2 P. falciparum strains were maintained in continuous long-term cultures in tissue culture medium. Cultures and assays were grown and conducted at 37° C. under a humidified atmosphere of 5% $CO_2$ and 5% $O_2$, with a balance of $N_2$ using either tissue culture medium or folic acid-free medium. Parasites at 1% parasitemia and 2% hematocrit were added to predosed 96-well plates and incubated for 72 h. Lysis buffer (20 mM Tris HCl, 5 mM EDTA, 0.008% saponin, and 0.08% Triton®-X with SYBR® green I dye was subsequently added to the plates and incubated for 1 h at ambient room temperature. Fluorescence was determined, and the plates were examined for relative fluorescence units (RFUs) per well. The drug concentrations were transformed and the data were then analyzed with Prism to yield drug 50% inhibitory concentrations (IC50s). Green D6, Green C235, and Green W2 are three strains in P. falciparum. W2 is chloroquine resistant and mefloquine sensitive, D6 is chloroquine sensitive but naturally less susceptible to mefloquine, C235 is resistant to mefloquine, chloroquine, and pyrimethamine.

Results

The data are provided in Tables 6-9 below.

TABLE 6

Anti-malarial data for pyrimidine IspF inhibitors.

| Designation | SYBR Green D6 $IC_{50}$ (uM) | SYBR Green C235 $IC_{50}$ (uM) | SYBR Green W2 $IC_{50}$ (uM) |
|---|---|---|---|
| HGN-0017 | >40 | >40 | >40 |
| HGN-0047 | >40 | >40 | >40 |
| HGN-0041 | >40 | >40 | >40 |
| HGN-0121 | 34.52 | >40 | >40 |
| HGN-0123 | ND | ND | ND |
| HGN-0125 | >40 | 19.68 | 16 |
| HGN-0038 | >40 | >40 | >40 |
| HGN-0119 | ND | ND | ND |

TABLE 6-continued

Anti-malarial data for pyrimidine IspF inhibitors.

| Designation | SYBR Green D6 IC$_{50}$ (uM) | SYBR Green C235 IC$_{50}$ (uM) | SYBR Green W2 IC$_{50}$ (uM) |
|---|---|---|---|
| HGN-0127 | >40 | >40 | 17.7 |
| HGN-0129 | 26.95 | 32.98 | 13.19 |
| HGN-0131 | ND | ND | ND |
| HGN-0117 | ND | ND | ND |
| HGN-0135 | ND | ND | ND |
| HGN-0133 | >40 | >40 | >40 |
| HGN-0113 | 29.29 | >40 | >40 |
| HGN-0111 | >40 | >40 | >40 |
| HGN-0115 | 17.45 | 27.58 | 17.59 |
| HGN-0016 | ND | ND | ND |
| HGN-0040 | >40 | >40 | >40 |
| HGN-0042 | >40 | >40 | >40 |
| HGN-0034 | >40 | >40 | >40 |
| HGN-0037 | >40 | >40 | >40 |
| HGN-0033 | >40 | >40 | >40 |
| HGN-0039 | >40 | >40 | >40 |
| HGN-0015 | >40 | >40 | >40 |
| HGN-0012 | ND | ND | ND |
| HGN-0077 | ND | ND | ND |
| HGN-0079 | ND | ND | ND |
| HGN-0011 | ND | ND | ND |
| HGN-0035 | ND | ND | ND |
| HGN-0050 | ND | ND | ND |
| HGN-0049 | 0.55 | 0.74 | 0.95 |
| HGN-0126 | >40 | >40 | >40 |
| HGN-0124 | ND | ND | ND |
| HGN-0122 | ND | ND | ND |
| HGN-0028 | >40 | >40 | >40 |
| HGN-0120 | ND | ND | ND |
| HGN-0118 | ND | ND | ND |
| HGN-0128 | ND | ND | ND |
| HGN-0130 | ND | ND | ND |
| HGN-0132 | ND | ND | ND |
| HGN-0136 | ND | ND | ND |
| HGN-0134 | ND | ND | ND |
| HGN-0114 | ND | ND | ND |
| HGN-0112 | ND | ND | ND |
| HGN-0116 | ND | ND | ND |
| HGN-0014 | >40 | >40 | >40 |
| HGN-0045 | >20 | >20 | >20 |
| HGN-0046 | ND | ND | ND |
| HGN-0036 | ND | ND | ND |
| HGN-0013 | >40 | >40 | >40 |
| HGN-0044 | >40 | >40 | >40 |

TABLE 7

Anti-malarial data for imidazole IspF inhibitors.

| Designation | SYBR Green D6 IC$_{50}$ (uM) | SYBR Green C235 IC$_{50}$ (uM) | SYBR Green W2 IC$_{50}$ (uM) |
|---|---|---|---|
| HGN-0029 and HGN-0056 | >40 | >40 | >40 |
| HGN-0018 | >40 | >40 | >40 |
| HGN-0019 | 11.3 | 13.3 | 13.6 |
| HGN-0020 | 4.2 | 7.2 | 5.6 |
| HGN-0137 | | | |
| HGN-0021 | 6.0 | 7.7 | 6.0 |
| HGN-0022 and HGN-0052 (HCl salt) | >40 | >40 | >40 |
| HGN-0048 | >40 | >40 | >40 |
| HGN-0091 | 3.175 | 4.874 | 3.526 |
| HGN-0090 | 5.797 | 6.153 | 3.943 |
| HGN-0094 | 8.876 | 9.116 | 6.221 |
| HGN-0108 | 11.48 | 13.81 | 7.219 |
| HGN-0051 | 1.7 | 3.4 | 0.59 |

TABLE 7-continued

Anti-malarial data for imidazole IspF inhibitors.

| Designation | SYBR Green D6 IC$_{50}$ (uM) | SYBR Green C235 IC$_{50}$ (uM) | SYBR Green W2 IC$_{50}$ (uM) |
|---|---|---|---|
| HGN-0096 | 9.798 | 12.92 | 7.898 |
| HGN-0092 | ND | ND | ND |
| HGN0098 | 10.16 | 14.38 | 8.381 |
| HGN-0099 | 5.362 | 5.436 | 4.251 |
| HGN-0100 | 4.275 | 9.366 | 5.647 |
| HGN-0109 | 4.798 | 5.735 | 3.163 |
| HGN-0106 | 3.001 | 3.524 | 4.099 |
| HGN-0093 | 5.829 | 6.345 | 3.36 |
| HGN-0095 | 6.1 | 6.594 | 4.048 |
| HGN-0097 | 10.16 | 5.178 | 2.12 |
| HGN-0107 | 5.653 | 7.291 | 4.088 |

TABLE 8

Anti-malarial data for fusion series IspF inhibitors.

| Designation | SYBR Green D6 IC$_{50}$ (uM) | SYBR Green C235 IC$_{50}$ (uM) | SYBR Green W2 IC$_{50}$ (uM) |
|---|---|---|---|
| HGN-0005 | >40 | >40 | >40 |
| HGN-0006 | ND | ND | ND |
| HGN-0007 | ND | ND | ND |
| HGN-0008 | ND | ND | ND |
| HGN-0102 | >40 | >40 | >40 |

TABLE 9

Anti-malarial data for miscellaneous IspF inhibitors.

| Designation | SYBR Green D6 IC$_{50}$ (uM) | SYBR Green C235 IC$_{50}$ (uM) | SYBR Green W2 IC$_{50}$ (uM) |
|---|---|---|---|
| HGN-0068 | 8.374 | 6.119 | 5.988 |
| HGN-0024 | >40 | >40 | >40 |
| HGN-0023 | 12.9 | >40 | >40 |
| HGN-0082 and HGN-0101 | >40 | >40 | >40 |
| HGN-0054 | 28.9 | >40 | 11.5 |
| HGN-0031 | >40 | >40 | >40 |
| HGN-0061 | 6.1 | 8.3 | 6.4 |
| HGN-0063 | >40 | >40 | >40 |
| HGN-0060 | 1.6 | 2.7 | 3.1 |
| HGN-0062 | 3.8 | 8.3 | 7.3 |
| HGN-0078 | | | |
| HGN-0080 | | | |
| HGN-0004 | >40 | >40 | >40 |
| HGN-0002 | >40 | >40 | >40 |
| HGN-0010 | >40 | >40 | >40 |
| HGN-0009 | >40 | >40 | >40 |
| HGN-0085 | >40 | >40 | >40 |
| HGN-0083 | 8.49 | 12.03 | 10.4 |
| HGN-0084 | >40 | >40 | >40 |
| HGN-0055 and HGN-0089 | 18.8 | >40 | 19 |
| HGN-0087 | >40 | >40 | >40 |
| HGN-0088 | >40 | >40 | >40 |
| HGN-0025 | >40 | >40 | >40 |
| HGN-0026 | >40 | >40 | >40 |
| HGN-0057 | 7.6 | 22.8 | 15.0 |
| HGN-0058 | >40 | >40 | >40 |
| HGN-0059 | >40 | >40 | >40 |
| HGN-0030 | >40 | >40 | >40 |

PUBLICATIONS

All publications cited in this application are herein incorporated by reference.

Begley et al. (2010) Chem. Biol. Drug Des. 76(3):218-233.
Brown, A. C., and Parish, T. (2008) BMC Microbiol. 8: 78.
Co et al. (2009) Antimicrob. Agents Chemother. 53:2557-2563.
Gershenzon, J., and Dudareva, N. (2007) Nat. Chem. Biol. 3: 408-414.
Hunter, W. N. (2007) J. Biol. Chem. 282; 21573-21577.
Kuzuyama, T. et al. (1999) Biosci., Biotechnol., Biochem. 63: 776-778.
Mayer et al. (1999) Angew Chem. Int. Ed. 38(12):1784-1788.
Piotto et al. (1992) J. Biomol. NMR 2(6):661-665.
Zhang, B. et al. (2011) Biochemistry 50: 3570-3577.

The invention claimed is:

1. A method of treating a bacterial infection in a mammal, the method comprising administering to the mammal a therapeutically effective amount of the compound of Formula I or Formula II

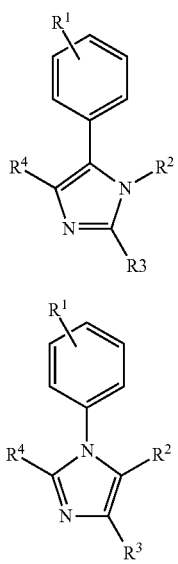

wherein
R$^1$ is OH or OR$^5$, wherein R$^5$ is lower alkyl, acyl, or CH$_2$OCOCH$_3$;
R$^2$ is alkyl, alkylaryl, arylheteroaryl, or heteroaryl;
R$^3$ is H or lower alkyl; and
R$^4$ is H or lower alkyl, or a pharmaceutically acceptable salt thereof.

2. The method of claim 1, further comprising administering at least one other antimicrobial agent.

3. A method of treating a protozoan infection in a mammal, the method comprising administering to the mammal a therapeutically effective amount of the compound of Formula I or Formula II

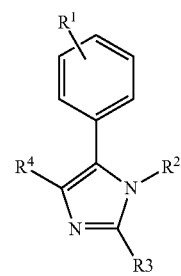

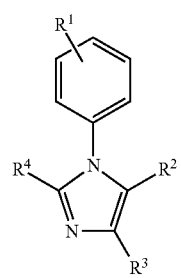

wherein
R$^1$ is OH or OR$^5$, wherein R$^5$ is lower alkyl, acyl, or CH$_2$OCOCH$_3$;
R$^2$ is alkyl, alkylaryl, arylheteroaryl, or heteroaryl;
R$^3$ is H or lower alkyl; and
R$^4$ is H or lower alkyl, or a pharmaceutically acceptable salt thereof.

4. A method for the treatment of bacterial, protozoan, and parasitic infections, the method comprising:
(a) obtaining a pharmaceutical composition comprising a therapeutically effective amount of the compound of Formula I or Formula II and a pharmaceutically acceptable carrier

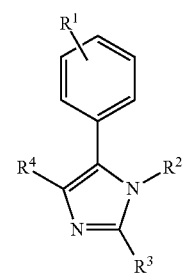

wherein
R$^1$ is OH or OR$^5$, wherein R$^5$ is lower alkyl, acyl, or CH$_2$OCOCH$_3$;
R$^2$ is alkyl, alkylaryl, arylheteroaryl, or heteroaryl;

$R^3$ is H or lower alkyl; and
$R^4$ is H or lower alkyl, or a pharmaceutically acceptable salt thereof; and
(b) administering the composition to a mammal in need thereof.

* * * * *